(12) United States Patent
Hlavinka et al.

(10) Patent No.: US 7,077,559 B2
(45) Date of Patent: Jul. 18, 2006

(54) CONTAINER OR BAG MIXING APPARATUSES AND/OR METHODS

(75) Inventors: Dennis J. Hlavinka, Arvada, CO (US); Michael A. Martinez, Golden, CO (US)

(73) Assignee: Gambro, Inc., Lakewood, CO (US)

( * ) Notice: Subject to any disclaimer, the term of this patent is extended or adjusted under 35 U.S.C. 154(b) by 109 days.

(21) Appl. No.: 10/425,281

(22) Filed: Apr. 28, 2003

(65) Prior Publication Data

US 2003/0214874 A1 Nov. 20, 2003

Related U.S. Application Data

(60) Provisional application No. 60/375,734, filed on Apr. 26, 2002.

(51) Int. Cl.
*B01F 11/00* (2006.01)
(52) U.S. Cl. .................... 366/197; 366/204; 422/44
(58) Field of Classification Search ............. 366/209, 366/210, 211, 212, 213, 218, 204, 220, 197; 604/416, 6.08; 435/173.1; 422/24, 44
See application file for complete search history.

(56) References Cited

U.S. PATENT DOCUMENTS

| | | | | |
|---|---|---|---|---|
| 2,845,929 A | * | 8/1958 | Strumia ................... 604/113 |
| 2,982,286 A | * | 5/1961 | Welch, Jr. ................. 604/245 |
| 3,518,393 A | * | 6/1970 | Barclay et al. ............ 219/772 |
| 3,539,156 A | * | 11/1970 | Zipperer .................... 366/110 |
| 3,735,964 A | * | 5/1973 | Lorenzen ................... 366/211 |
| 3,819,158 A | * | 6/1974 | Sharpe et al. .............. 366/349 |
| 4,608,255 A | | 8/1986 | Kahn et al. |
| 4,726,949 A | | 2/1988 | Miripol et al. |
| 4,750,845 A | * | 6/1988 | Nabetani ................... 366/208 |
| 4,866,282 A | | 9/1989 | Miripol et al. |
| 4,880,788 A | * | 11/1989 | Moake et al. ............. 514/150 |
| 4,952,812 A | | 8/1990 | Miripol et al. |
| 5,030,200 A | | 7/1991 | Judy et al. |
| 5,184,020 A | | 2/1993 | Hearst et al. |
| 5,290,221 A | | 3/1994 | Wolf, Jr. et al. |
| 5,304,113 A | | 4/1994 | Sieber et al. |
| 5,459,322 A | | 10/1995 | Warkentin |
| 5,567,616 A | * | 10/1996 | Dill, II ..................... 366/220 |
| 5,683,661 A | | 11/1997 | Hearst et al. |
| 5,762,867 A | | 6/1998 | D'Silva |
| 5,854,967 A | | 12/1998 | Hearst et al. |
| 5,868,695 A | | 2/1999 | Wolf, Jr. et al. |
| 5,922,278 A | | 7/1999 | Chapman et al. |
| 5,951,509 A | | 9/1999 | Morris |
| 6,142,661 A | * | 11/2000 | Lafond ..................... 366/204 |
| 6,190,609 B1 | | 2/2001 | Chapman et al. |
| 6,258,319 B1 | | 7/2001 | Hearst et al. |

(Continued)

FOREIGN PATENT DOCUMENTS

EP 0132632 2/1985

(Continued)

*Primary Examiner*—Tony G. Soohoo
(74) *Attorney, Agent, or Firm*—Laura B. Arciniegas; Edna M. O'Connor; John R. Merkling

(57) ABSTRACT

A mixing system, apparatus and/or method. Pathogen reduction of and/or mixing storage solutions into blood or blood components are useful purposes for these. Squeezing or clapping devices may be used to activate the mixing process, as may rotational devices or laterally movable, rotational and/or orbital devices. Constriction elements may also be used to create useful vortex mixing actions. Photoradiation may be provided while the components continue to be mixed together for pathogen reduction of blood or blood components.

24 Claims, 20 Drawing Sheets

U.S. PATENT DOCUMENTS

| | | |
|---|---|---|
| 6,258,577 B1 | 7/2001 | Goodrich et al. |
| 6,267,498 B1 * | 7/2001 | Lafond et al. ............... 366/204 |
| 6,277,337 B1 * | 8/2001 | Goodrich et al. ........ 422/186.3 |
| 6,369,394 B1 * | 4/2002 | Lee ....................... 250/455.11 |
| 6,433,343 B1 | 8/2002 | Cimino et al. |
| 6,461,567 B1 | 10/2002 | Hearst et al. |
| 6,565,802 B1 | 5/2003 | Hanley et al. |
| 6,586,749 B1 | 7/2003 | Cimino et al. |
| 6,634,783 B1 * | 10/2003 | Baron ........................ 366/204 |
| 2001/0024623 A1 | 9/2001 | Grimm et al. |
| 2003/0062483 A1 | 4/2003 | Cimino et al. |

FOREIGN PATENT DOCUMENTS

| | | |
|---|---|---|
| EP | 0240152 | 10/1987 |
| FR | 2686255 | 7/1993 |
| WO | WO 99/43790 | 9/1999 |
| WO | WO99/59645 | 11/1999 |
| WO | WO00/74806 | 12/2000 |
| WO | WO 02/26270 | 4/2002 |

* cited by examiner

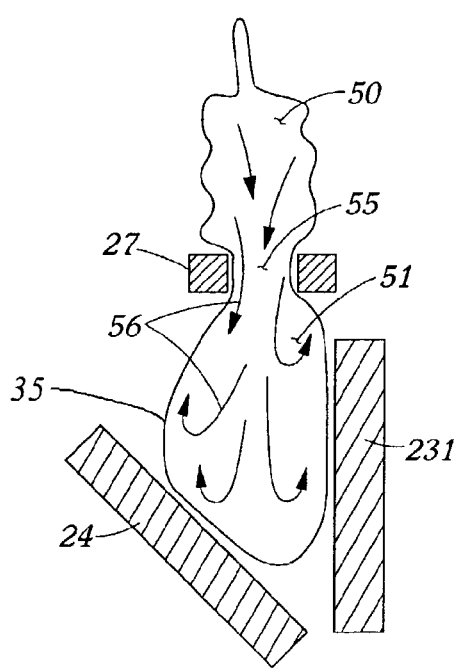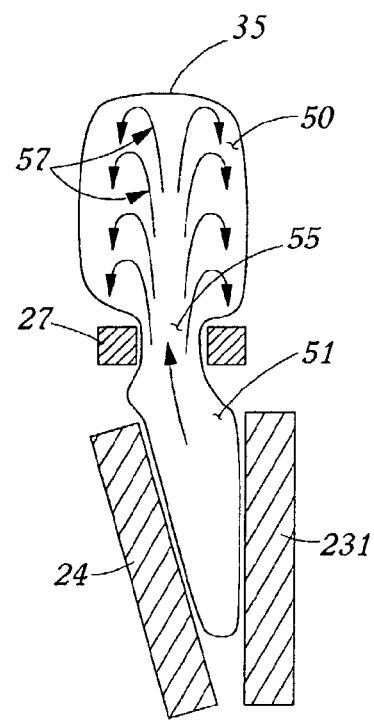
FIG. 7        FIG. 8
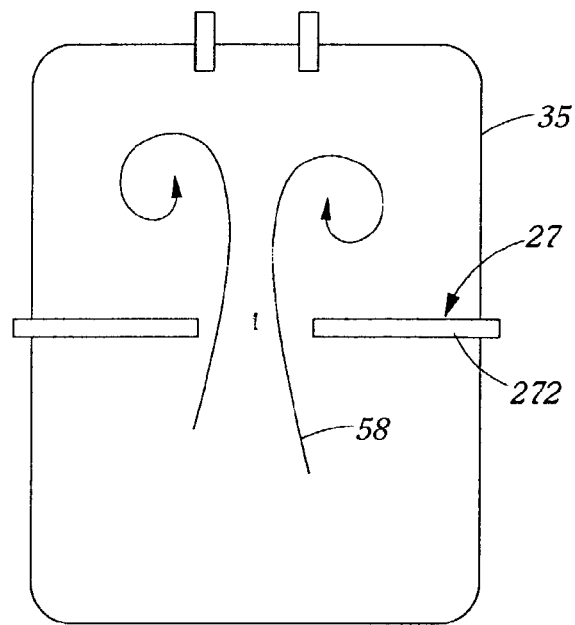
FIG. 9

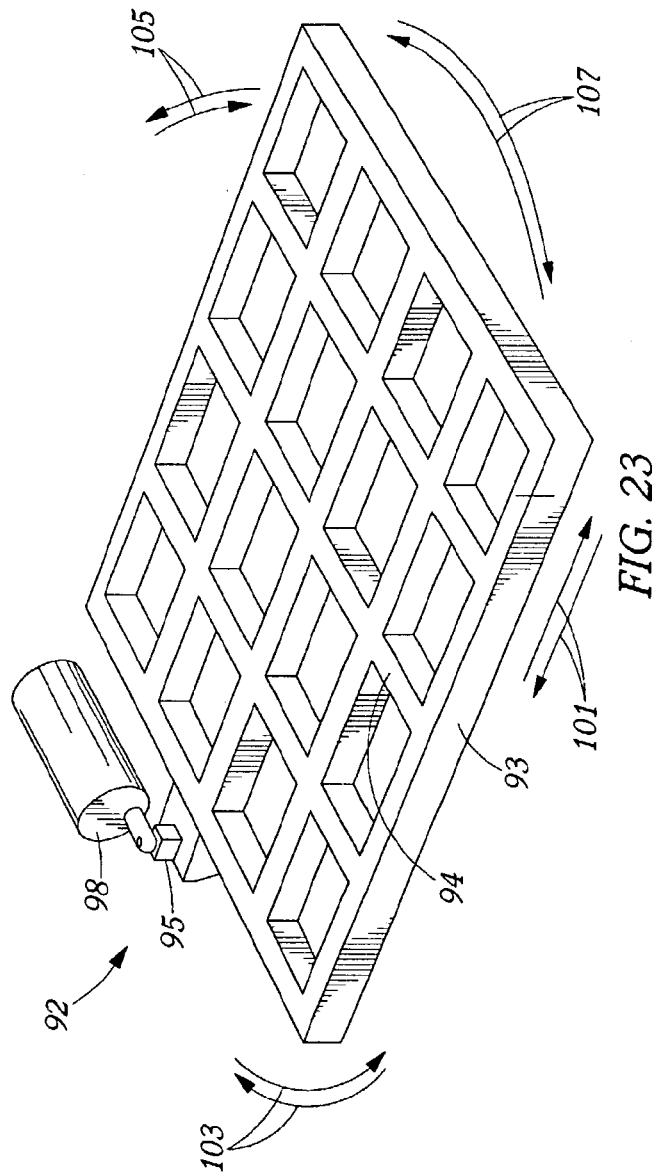
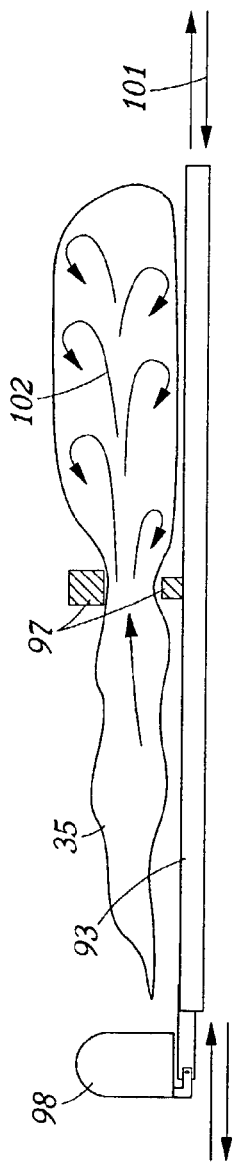
FIG. 23
FIG. 24

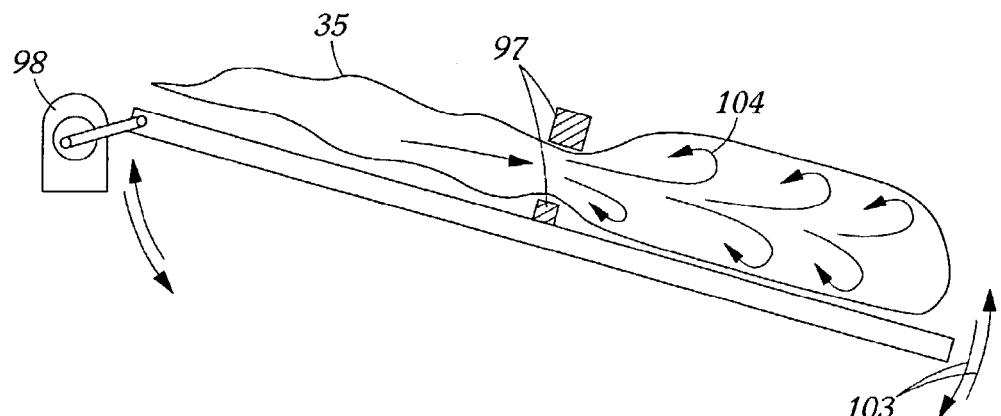
FIG. 25
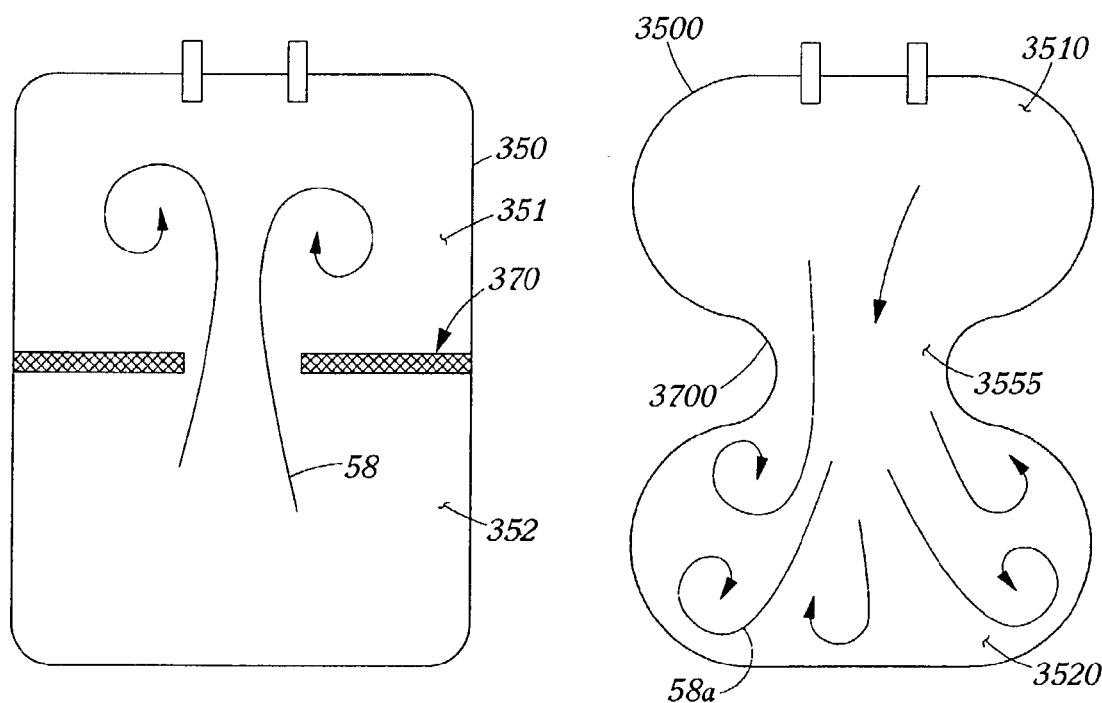
FIG. 26
FIG. 27

CONTAINER OR BAG MIXING APPARATUSES AND/OR METHODS

PRIORITY CLAIM

This application claims priority from U.S. Provisional application No. 60/375,734, filed Apr. 26, 2002.

FIELD OF THE INVENTION

This invention is generally related to apparatuses and/or methods for mixing the contents of various containers or bags while the contents are being irradiated. Of particular note is the use of these apparatuses and methods in a pathogen reduction procedure.

BACKGROUND

Contamination of human blood and blood components with pathogens such as human immunovirus (HIV), hepatitis and/or bacteria create a serious risk for patients who receive blood or blood components via blood transfusions.

To help combat the problem of pathogenic contamination in blood and/or blood components, one method of reducing pathogens in blood and biologically useful fluids may be to use radiation to substantially destroy any pathogens contained in the fluid. Radiation may be used to inactivate pathogens contained in blood and blood components by generating mutagenic alterations in their genetic material. Above a minimum dose of radiation, the pathogens lose their capacity to reproduce. Radiation damages the nucleic acids of the pathogens by creating intrastrand nicks and inducing nucleotide photodimerization, both of which disrupt nucleic acid replication. Through such mechanisms, irradiating blood and blood components with either visible or ultraviolet (UV) light can be an effective means for reducing undesirable pathogens within blood and other biologically useful fluids.

Unfortunately, the energy of short wavelength UV light may also damage the blood and blood components that are the desired end-products of the irradiation process. Thus, an inherent problem in the application of UV-irradiation techniques is controlling the irradiation of the fluid so as to ensure sufficient radiation exposure to reduce undesirable pathogens within a fluid while at the same time minimizing or eliminating damage to the biologically useful fluids. One way to avoid substantial damage to the biologically useful fluid by UV light is to design an apparatus which will effectively mix the fluid in such as way so as not to over-expose the fluid to the radiation.

Blood and blood components can also be decontaminated using pathogen reducing agents or photosensitizers which, when activated, also reduce pathogens contained in the blood or other biologically useful fluids but does not destroy the biological activity of the blood or blood component product.

Pathogen reduction agents, which may be used with this invention, include the class of photosensitizers known in the art to be useful for reducing pathogens. A "photosensitizer" as defined here is any compound which absorbs radiation of one or more defined wavelengths and subsequently transfers the absorbed energy to an energy acceptor. Thus, such photosensitizers may be activated by the application of electromagnetic spectra (e.g., UV and visible light) to then reduce certain pathogens with which they may interact.

Various photosensitizers have been proposed for use as blood or blood component additives to inactivate pathogens in body fluids. Examples of non-endogenous photosensitizers that have been proposed for use as blood or blood component additives include porphyrins, psoralens, acridines, toluidines, flavins (acriflavin hydrochloride), phenothiazine derivatives, coumarins, quinolines, quinones, anthroquinones and dyes such as neutral red and methylene blue.

Other categories of photosensitizers are endogenous pathogen reduction agents, such as 7,8,10-trimethylisoalloxazine (lumiflavin), 7,8-dimethylalloxazine (lumichrome), isoalloxazine-adenine dinucleotide (flavin adenine dinucleotide [FAD]), alloxazine mononucleotide (flavin mononucleotide [FMN] and riboflavin-5-phosphate), vitamin K and vitamin L and their metabolites and precursors, napthhoquinones, naphthalenes and naphthols as well as their derivatives. One preferred example of an endogenous photosensitizer contemplated for use with this invention is an alloxazine such as 7,8-dimethyl-10-ribityl isoalloxazine, commonly known as riboflavin. An advantage of using endogenous photosensitizers to reduce blood contaminants is that endogenous photosensitizers are not inherently toxic to the blood cells and if photoactivated do not yield toxic photoproducts after exposure to radiation. Therefore, a removal or purification step is not required after the decontamination process, and the treated product can then be stored in the same solution used in the pathogen reduction process, transfused into a patient, or returned directly to the donor.

One method of decontaminating blood or blood components using a photosensitizer includes mixing an effective amount of a photosensitizer with the fluid to be decontaminated in a batch-wise way; then exposing the fluid to an amount of photoradiation at an appropriate wavelength sufficient to activate the photosensitizer and allow the activated agent to interfere with the pathogens contained within the fluid such that the pathogens contained in the fluid are reduced. The wavelength of light used will depend on the photosensitizing agent selected as well as the type of blood components being pathogen reduced. The light source or sources may provide light in the visible range, the ultraviolet range, or a mixture of light in both the visible and the ultraviolet range Decontamination or pathogen reduction systems may be designed as stand-alone units as described above, or may be incorporated into existing apparatuses known to the art for separating or treating blood to be withdrawn from or administered to a patient. For example, such blood-handling apparatuses include the COBE Spectra™ or TRIMA® apheresis systems, available from Gambro BCT Inc., Lakewood, Colo., as well as apheresis systems of other manufactures. The decontamination system may be inserted before the collected blood is separated into components. Alternatively, the decontamination system may be inserted downstream of the point where the blood is separated and/or collected, or at any point after separation of blood constituents. It may even be inserted just prior to reinfusion of the blood product back into the patient. It is further understood that discrete irradiation sources could be placed upstream from the collection points of each separated blood component, such as red blood cells, platelets, and plasma. The use of three separate blood decontamination systems, one for each separated blood component, may be preferred to placement of a single blood decontamination system upstream of the blood separation vessel of an apheresis system because the lower flow rates in the separated component lines may allow for greater ease of irradiation.

In other embodiments, decontamination systems for use in and/or with the present invention may be used to process previously collected and/or stored blood products, whole blood or components, in a batch-wise way, as discussed above, and in further detail below. In some photosensitizer methods, the blood product to be decontaminated is flowed through an entry port into a photopermeable bag or other container. The term "photopermeable" means that the material of the container is adequately transparent to photoradiation.

Polymeric bags and like containers, flexible or otherwise, which are commonly used to collect and store blood and blood components, are useful as the photopermeable containers referred to above.

After the pathogen reduction process, the pathogen reduced fluid may then be flowed out of the photopermeable container into a storage container through an exit port, or may be stored in the same photopermeable container used in the photoinactivation process until transfused into a patient.

One problem with the use of light alone or light in combination with a photosensitizer to reduce pathogens in blood or blood products, is that during the pathogen reduction process, a portion of the fluid to be pathogen reduced may become trapped within dead spaces or opaque portions of the bag or container. Fluid trapped in these dead spaces or opaque portions may not be reached by light and may therefore still contain pathogens which will re-infect the fluid which was previously pathogen reduced.

Another problem in pathogen reducing fluid using light results from the laminar nature of fluid flow in a container. In either a flow-through or a batch wise system, a parabolic velocity profile exists for the fluid contained in either the fluid-flow channel or a self contained bag. Upon agitation or application of a force, the fluid at the center of the flow channel or bag is traveling at a maximum velocity, while the fluid close to the walls at the bag-fluid interface remains nearly stationary. Because of this flow profile, upon irradiation of blood or blood components, the exposure time of the blood is the shortest for the blood traveling at maximum velocity at the center of the container, and increases for successive portions of the flow profile moving outwardly from the center. Therefore, not all of the blood in a bag is irradiated at the same intensity and for the same length of time. In addition to the velocity profile, blood tends to spread in a thin film along the surface of the bag due to surface tension and the tendency of blood to cling to the bag's surface. In the absence of vigorous agitation, the blood located along the walls of the container would have an extremely long residence time. Thus, the blood or blood component nearest the walls (closest to the irradiation source) runs the risk of being overexposed to radiation which may significantly damage the blood or blood components, while the fluid in the middle of the container runs the risk of being under irradiated, thus any pathogens contained in this region would receive little or no radiation, and would be likely to re-contaminate the fluid with still viable pathogens.

In view of the above background, it can be seen that there is a need for a method and apparatus for pathogen reducing a fluid that ensures adequate exposure of all of the fluid to radiation while simultaneously minimizing the damage to the blood or blood components.

SUMMARY OF THE INVENTION

The present invention relates to methods, systems and apparatuses for mixing various fluid (or other substance) elements. More particularly, the present invention applies desirably to the preparation including mixing of a blood or blood component product in a pathogen reduction procedure. In one embodiment, the apparatus comprises a support structure for hanging a flexible polymeric container or bag therein or thereon and a moveable "clapper" structure which alternately squeezes the bag and releases the bag to mix the contents thereof. A clamp-like structure may also be provided to create one or more constrictions in the bag to provide mixing vortices within the bag to enhance the exposure of the bag contents to or adjacent the internal surface of the bag and thus also to any photoradiation impinging thereon. Photoinactivation is thus enhanced particularly for relatively opaque fluids (such as RBCs). A photosensitizer may be added to the blood or blood component to be pathogen inactivated and then thoroughly mixed therein. Then, also or alternatively the mixing effect could be sustained during illumination of the product therein.

Another embodiment involves a rotating structure in which a flexible bag may be disposed such that when rotated, the contents of the bag are continually rotated up and alternately pulled down by gravity. Rotating embodiments may also have light illumination and/or clamp-like structures constricting portions of the bag to create vortices which enhance mixing.

BRIEF DESCRIPTION OF THE DRAWINGS

FIG. 7 shows a partial cross-sectional view of a bag and clamp assembly as in FIG. 6.

FIG. 8 shows another partial cross-sectional view of a bag and clamp assembly as in FIG. 6.

FIG. 9 shows an elevational schematic view of a flexible container and clamp assembly.

FIG. 23 is an isometric view of a part of the embodiment of FIG. 22.

FIG. 24 shows a partial cross-sectional view including fluid vortices created within a bag used in an embodiment like that shown in FIG. 22 upon application of a force causing the fluid to flow in the general direction of the lateral pointing arrows.

FIG. 25 shows a partial cross-sectional view including fluid vortices created within a bag used in an embodiment like that shown in FIG. 22 upon rotation in the direction of the arrows.

FIG. 26 shows a plan view of an alternative bag for containing fluid to be mixed according to the present invention.

FIG. 27 shows a plan view of an alternative bag for containing fluid to be mixed according to the present invention.

DETAILED DESCRIPTION

Figure 1:
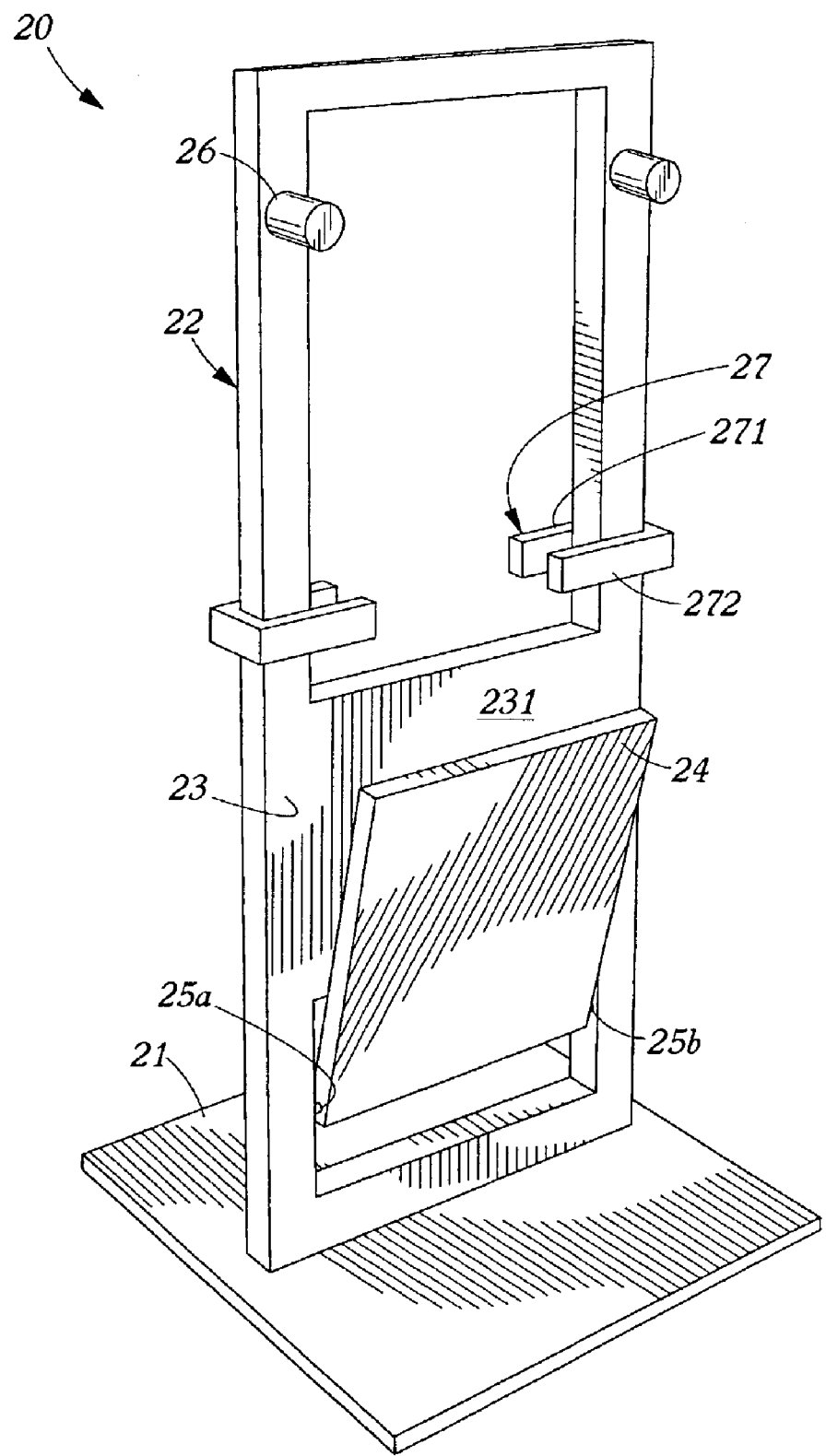
FIG. 1 is a schematic isometric view of one embodiment of a mixing system according to the present invention.

FIG. 1 shows a blood or blood component mixing system 20 for mixing blood components in accordance with the present invention. Whole blood is withdrawn from a donor/patient (not shown) and may be treated in whole blood form by the present invention, or it may be provided to an apheresis system or other type of blood component separation device (not shown) often of a centrifugal type, where the blood may be separated into one or more of various component types and at least one of these blood component types can then be removed/collected as a product from the separation device. The blood or blood component products (e.g., platelets, plasma, white blood cells, or red blood cells) may then be pathogen reduced either continuously in a flow-through manner within or adjacent the apheresis machine (not shown) or in a separate batchwise step. Ultimately, the pathogen reduced blood components may then be stored for later transfusion into a patient.

Figure 2:
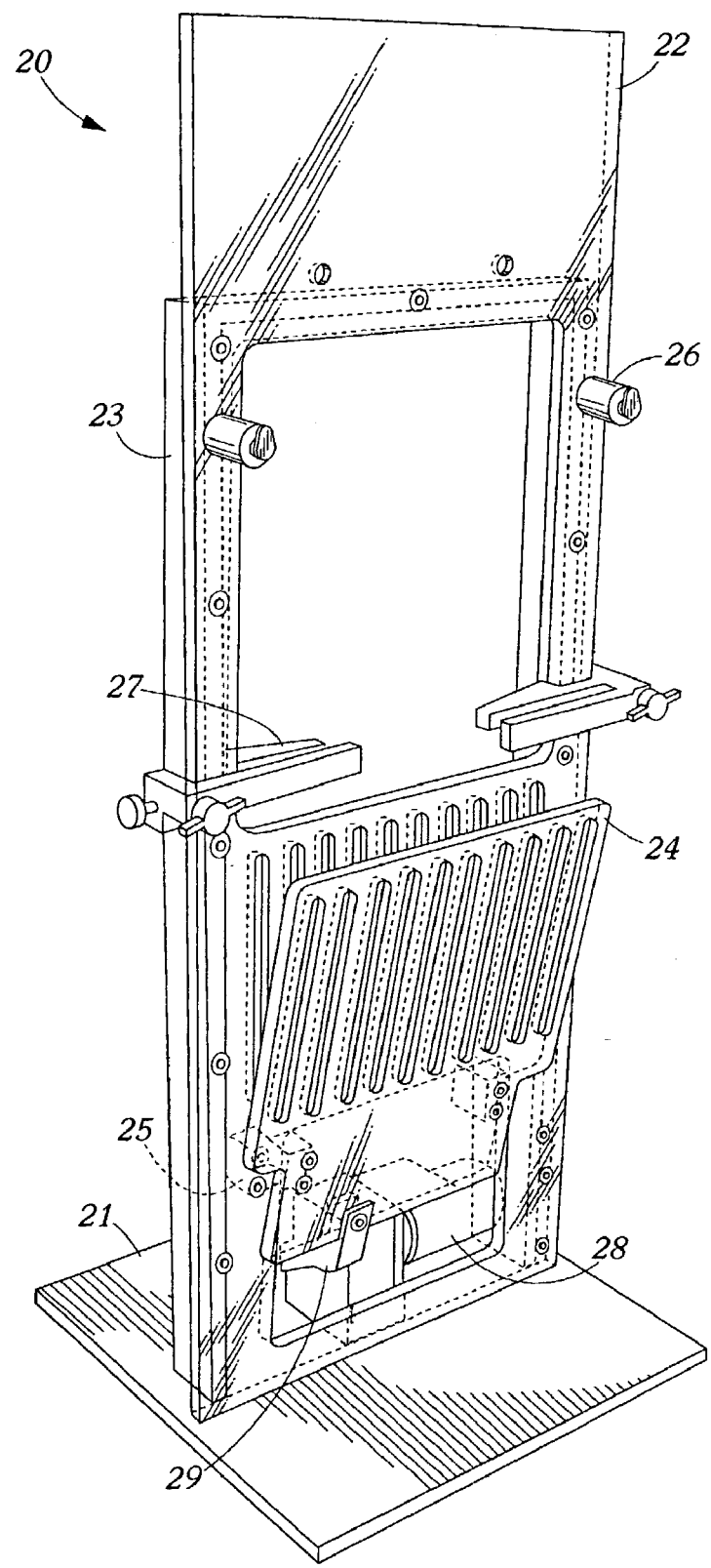
FIG. 2 is another isometric view of an embodiment of a mixing system according to the present invention.
Figure 3:
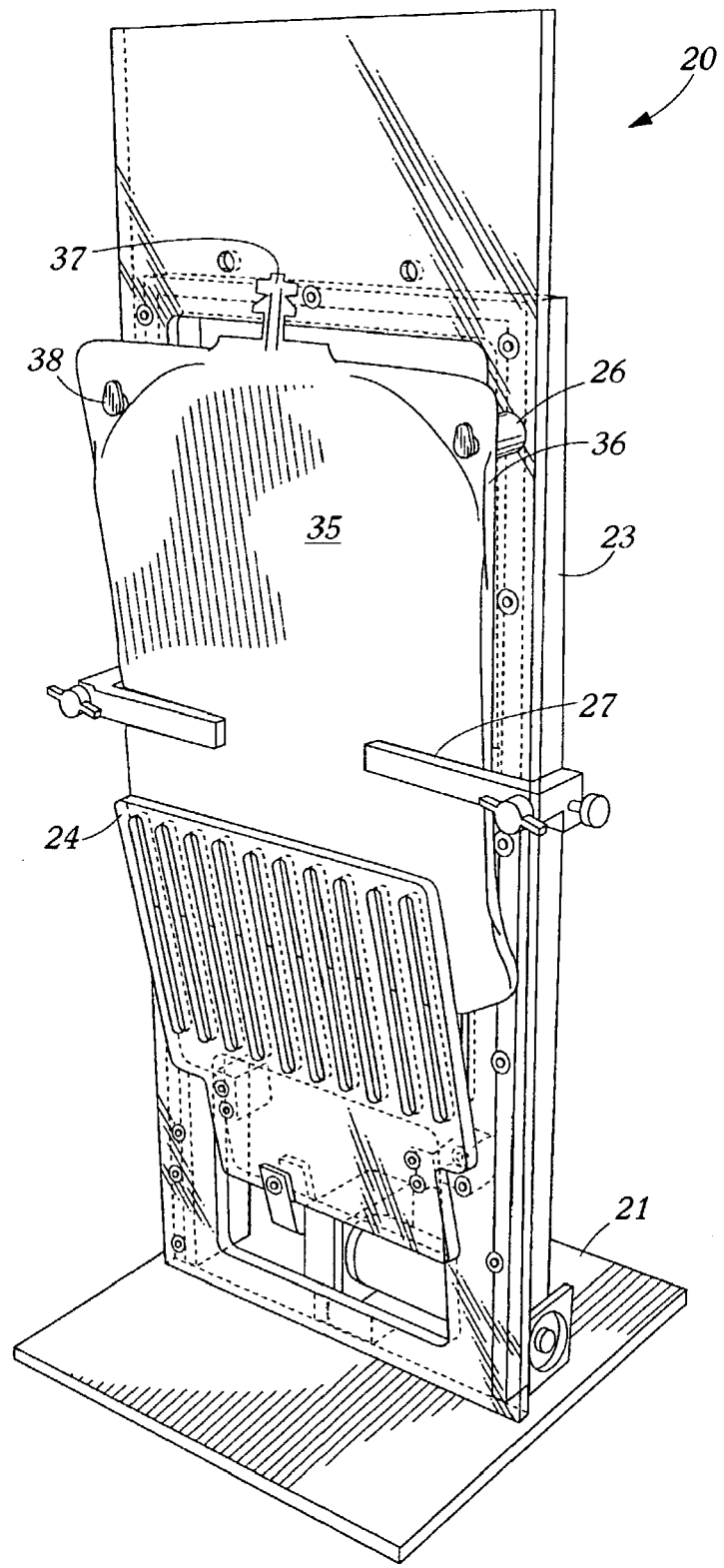
FIG. 3 shows an isometric view of a flexible container and a mixing assembly according to one embodiment of the present invention.
Figure 4:
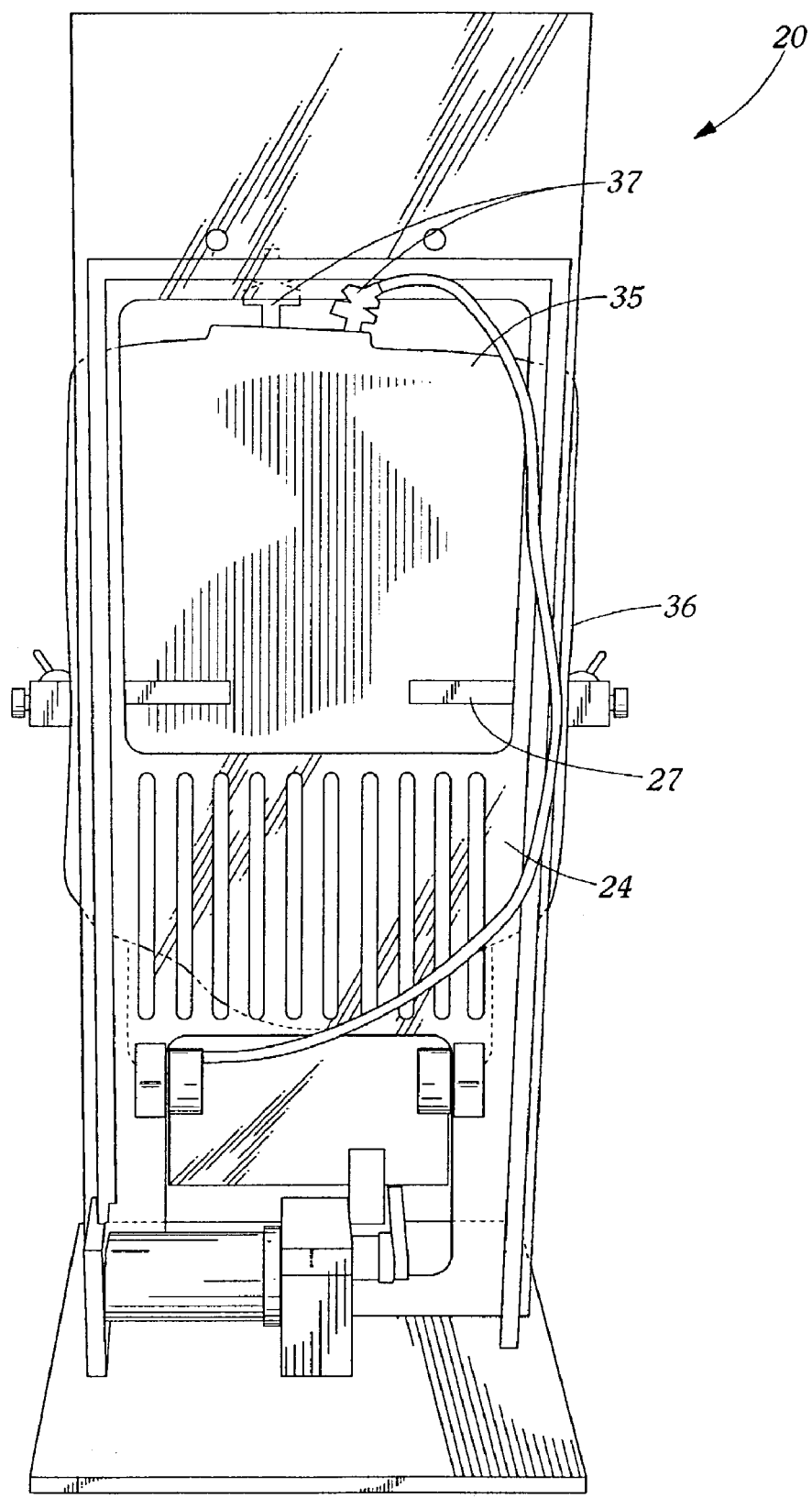
FIG. 4 shows a substantially elevational view of a flexible container and a mixing assembly according to the embodiment of FIG. 3.

The system 20 shown generally in FIG. 1 includes a mixing device 22 (shown schematically here) which has a support structure generally designated 23 disposed on a base 21. A moveable "clapping" member 24 is disposed in operative relation to support 23, and as shown here, has a pivotable relationship therewith as depicted in FIG. 1 by the connection through pins 25 (see pins 25a and 25b). As shown in FIGS. 2–4, moveable member 24 has openings or slots disposed therein. Such openings or slots may be used to allow radiation to penetrate the bag 35 (see FIG. 3) which may be contained therein, or may be used to allow heat generated during the irradiation process to escape so as not to damage the blood or blood product being irradiated. Support structure 23 also may have, as shown, one or more devices for holding a container therein such as the two holding members 26 which may be, as shown here, protrusions or hooks on which a bag may be hung (see below). Also shown schematically are two clamp-like constriction elements 27, the use of which for creating mixing vortices will be described further below.

An exemplar device 22 is shown in more detail in FIGS. 2–4. One additional detail reflected herein is a motor 28 connected to movable member 24 via a linkage connection 29. Motor 28 provides the motive force to move the movable member 24 as will be described further below. FIG. 3 also shows a flexible container or bag 35 disposed in/on device 22 as supported by hanging members 26.

Figure 5:
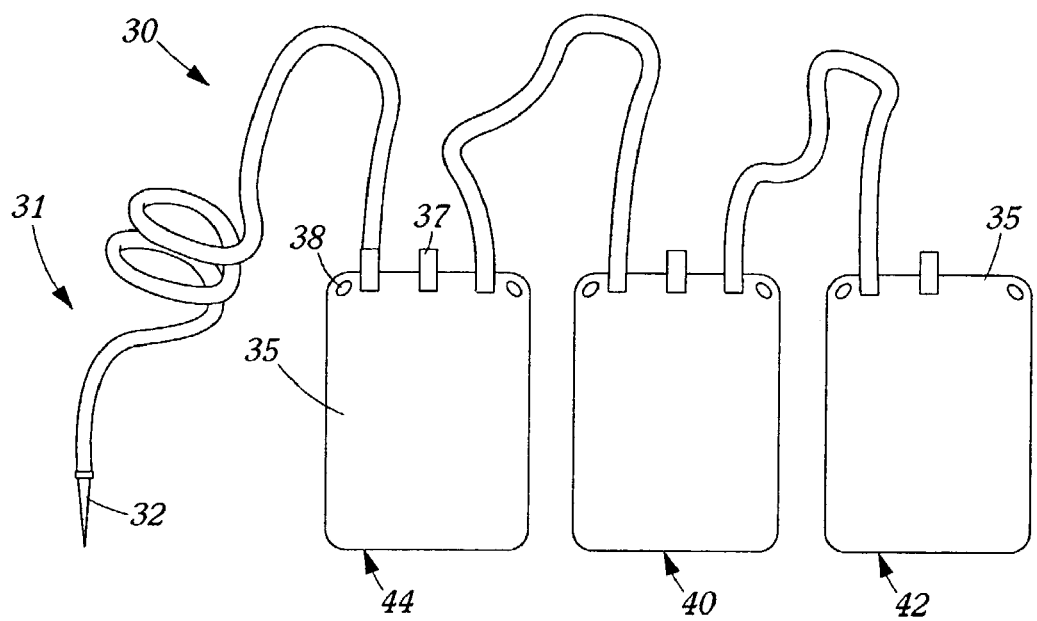
FIG. 5 illustrates an extracorporeal tubing and bag assembly which may be used with and/or in a system of the present invention.

FIG. 5 is but one example of a preconnected extracorporeal tubing circuit 30 which may be used to obtain a blood product according to known (or to be developed) methods. In general, a blood removal/inlet tubing sub-assembly 31 provides a needle 32 to interface a donor (not shown) with the remainder of the tubing circuit 30. A platelet collection tubing and bag assembly 40, a plasma collection tubing and bag assembly 42, and a red blood cell collection tubing and bag assembly 44 may also be connected within circuit 30. As will be appreciated, this is but one example of an extracorporeal tubing circuit 30 and further various blood component assemblies (more or less than shown) are or may be pre-interconnected to combinatively yield a closed, pre-sterilized disposable assembly suitable for a one time use. Any of these bags 35 may then be used in system 20, as well as any of the other systems described herein below.

Most portions of the tubing assemblies 30, 40, 42 and 44 including bags 35 may be made from flexible polymeric or plastic components including, for example, polyolefin or polyvinyl chloride (PVC) tubing lines and bags 35, that preferably permit visual observation and monitoring of blood/blood components therewithin during use, as well as for irradiation purposes. All tubing lines and bags may be preconnected before sterilization of the entire disposable assembly to assure that maximum sterility of the system is maintained. Thus, bag 35 may be pre-connected and/or post-connectable with the extracorporeal tubing circuit 30 as described relative to FIG. 5 above, or may be used separately, as a stand alone apparatus, neither alternative departing from the spirit and scope of the invention. Note further that alternative resilient or even rigid containers may also be used in some embodiments of the present invention.

In any case, FIGS. 3 and 4 show any of the FIG. 5 flexible polymeric containers or bags 35 disposed in a mixing structure 22 of a system 20 in accordance with the present invention. The container or bag 35 may be made of a flexible polymeric type film which is sealed or welded around its outer border zones during manufacture to form pre-formed seals or welds (see weld 36 denoting the circumference of container or bag 35). The seals or welds 36 create a fluid tight, sealed interior space or main body compartment (not separately shown in FIGS. 3–4). Ports or openings 37 allow fluid ingress and/or egress into and/or out of the container or bag 35. As shown in FIGS. 3–4, two ports 37 may be located on the same side of the container or bag 35. Such a container or bag 35 could contain one, two or more ports as is generally known. Known types of ports may be used in this invention, including one or more ports having a frangible-type closure mechanism (not shown).

As shown in FIG. 3, the container or bag 35 may have a hole or holes 38 punched in for example, the upper or lower edges of the preformed factory seal 36 to mount the container or bag 35 in a hanging position as will be described further. Alternatively, the bag may not have holes punched in the pre-formed factory seal (see FIG. 4) and then may be hung in various other fashions, as for example, using clamps (not shown). The container or bag 35 may be hung before, during or after the process of combining the blood component with any additive solutions, if used, into the bag 35. The pre-formed factory seal 36 or any of the other pre-formed seals may also be made wide enough so that a label describing the contents of the bag 35 may preferably be placed on the area over the seal (not shown). The bag 35 may also have a connection to a sample bulb via a port (not separately shown) to allow for fluid removal and sample testing or the like. A port which allows for the connection of a spike receptor (not shown) or to enable the sterile docking of a further bag or tube for the addition of a photosensitizer or blood component may also be added to container or bag 35. A spike connector (not shown) may also preferably include a sterile barrier filter as is known in the art.

In one embodiment, and as introduced above and further described below, an external constriction element or clamp assembly 27 on or otherwise associated with (or dissociated from) device 22 may be a clamp, a clip, or anything of the like which may be removably connected to the container and thus divides a single container into multiple removable sub-compartments by a restricted flow area (though preferably still allowing flow therethrough) and limits fluid communication between each of the separate sub-compartments. More constriction elements than specifically shown in the figures may be used to create more than the two general sub-compartments shown in a single container as well. Alternatively, pre-formed seals or welds (not shown) may be made in container 35 to create one or more sub-compartments with constricted flow areas, yet permitting flow between compartments. Bags containing sub-compartments made with pre-formed seals or welds may be used alone or in combination with clamp assembly 27. United States Patent Application US 2002/0138066, published Sep. 26, 2002 and herein incorporated by reference in its entirety to the amount not inconsistent, discloses containers having multiple pre-formed subcompartments made with seals or welds which may be used with the present invention.

FIGS. 1–3 show isometric views of clamp assemblies 27 (not shown with container or bag 35 in FIGS. 1 and 2, but shown therewith in FIG. 3) according to the present invention. Each clamp assembly 27 preferably includes at least one bar 271 (see FIG. 1), and as shown, preferably a second bar 272. As will be described, these bars 271, 272 assist in creating a narrowed fluid passage in container 35 between the sub-compartments formed by the clamp assemblies 27.

Figure 6:
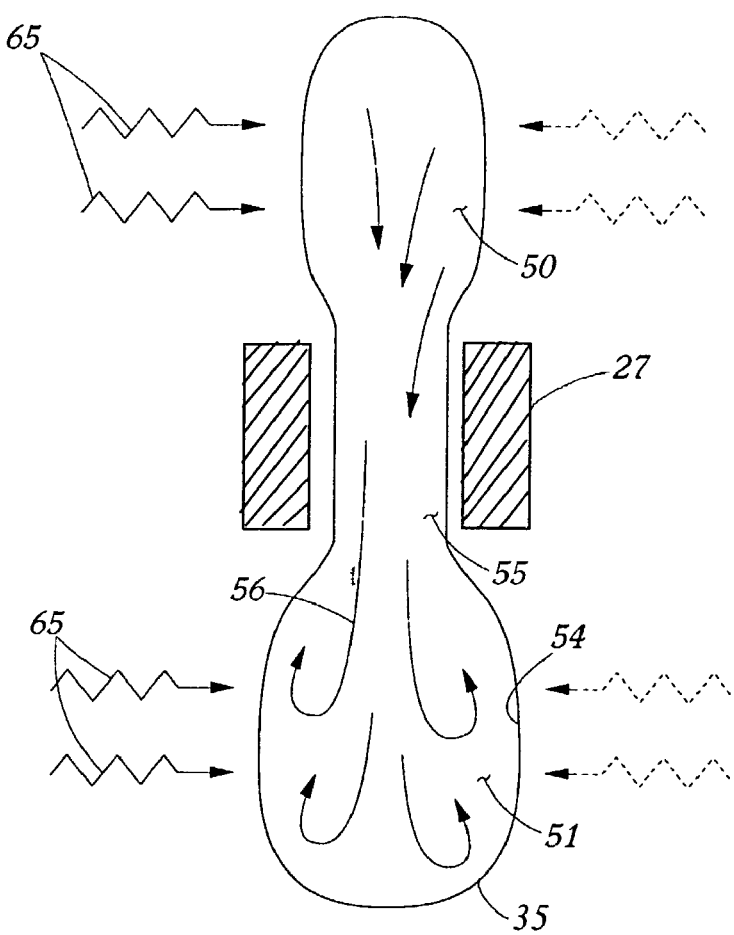
FIG. 6 shows a partial cross-sectional view of a bag and clamp assembly.

FIG. 6 shows a partially broken away cross-sectional view of a clamp assembly 27 (shown in dashed lines) creating separate sub-compartments 50 and 51 in a flexible container or bag 35. The clamp assembly 27 creates a temporary, preferably removable constriction 55 along all or part of the width of the bag to create the two distinct sub-compartments 50 and 51. The clamp assembly 27 may, in one embodiment, be easily removed from the container or bag 35 (as described below) to create a single bag with only one internal compartment. This may be achieved by simply loosening and/or removing the bar(s) 271, 272 on/from the device 22. Once the bars 271, 272 are loosened or removed, the bag 35 may be removed from the structure 22 by removing the bag 35 from the hooks 26 (if applicable). In an alternate embodiment, clamp assembly 27 may not need to be removable or loosenable from device 22. Clamp assembly 27 may be permanently affixed to device 22, and bag 35 may be slid in and out of the clamp assembly 27.

One method of using the above-described embodiments is as follows, described in relation to the embodiment of FIGS. 1–4 as shown by FIGS. 6, 7 and 8. Although not specifically described, the method may also be used generally with the alternative embodiments described below. Initially, blood or blood components to be pathogen reduced are disposed in bag 35. Any other components which may be desirable for the pathogen reduction procedure such as a photosensitizer may be further disposed in bag 35, or may be prepackaged in a satellite bag assembly (not shown). Any number of other solutions containing other necessary components for pathogen reduction or other purposes such as storage of blood or separated blood components may be added to bag 35 through port 37 at any desirable time. Note, the additional components may be in a dry solid or a liquid form.

In one use of the invention, solutions for the pathogen reduction and/or storage of blood and/or blood components may be preliminarily mixed together or may be simultaneously mixed with the blood product to be pathogen reduced. After combination of the fluids either before or after addition to the blood or blood component product to be pathogen reduced, the blood or blood component to be pathogen reduced and the solution which may contain a photosensitizer are mechanically mixed together using a mixing structure 22 according to the present invention. The mixture may be exposed to a light source while continuing the mixing process.

FIG. 6 shows the creation of multiple vortices within a flexible polymeric bag similar to the type described in FIGS. 3, 4 and 5, when disposed in operative relationship with a clamping device, such as device 27. Because of the flexible nature of the bag 35, clamp 27 causes a partial constriction which may be located approximately halfway up the length of the bag and as shown in FIGS. 1–4 each clamp 27 may extend inwardly from the sides of the container/bag 35. As shown in FIGS. 6, 7 and 8, the created narrowed or constricted portion 55 in the sides of the container 35 acts as follows. In the first instance, gravity pulls the fluid down from the upper compartment 50, through the constriction 55 and then into the lower compartment 51. This is shown generally in FIGS. 6 and 7. Flow vortex action is shown by the flow arrows 56, which help reach and "scrub" the interior surfaces 54 of the bag 35. Such mixing action helps to replace the fluid located along the fluid-bag surface interface 54 with fluid from the interior of the bag. Such turn over of fluid helps to prevent overexposure of the fluid nearest the bag surface 54 (and nearest to the irradiation system) to radiation, and helps bring fluid from the interior of the bag 35 to the surface to be irradiated. Although such "scrubbing" action is described in relation to fluid vortices generated by the mixing process, random flow mixing will also work to facilitate fluid turn over. Then, in the second instance, as shown by FIG. 8 and upon the application of a force or pressure to the bag, such as by squeezing of the lower bag portion 51 by the moveable member 24, the fluid within the container 35 may be forced to move to the upper portion 50 from the lower portion 51 of the container 35 through the narrowed portion 55 created by the clamp(s) 27. Moveable member 24 is shown in FIG. 7 in a relative open position relative to a back wall 231 (see FIG. 1) of a device 22, whereas moveable member 24 is shown moved in FIG. 8 to a relative closed position adjacent wall 231 between which the bag 35 has been squeezed thereby providing the force that moved the fluid up from the lower compartment 51 to the upper compartment 50. This force also caused the flow vortices 57 which scrub the upper inner walls 54 of bag 35. This movement creates vortices within the fluid as shown in FIG. 8 which helps to further mix the fluid. Although a force application and resultant vortices shown in FIG. 8 are shown as being directed towards the upper portion of bag 35 respectively, the force application and resultant vortices could be directed to either the upper portion or the lower portion of the bag 35 or both, depending upon the squeezing or relaxing of the device 22. In a relatively substantially vertically disposed system 20, the fluid within the bag 35 may be repeatedly forced to flow to the upper portion 50 of the container by action of device 22 and then allowed to be pulled to the lower portion by gravity to ensure thorough mixing of the blood or blood component product and a photosensitizer (if added) as well as ensuring thorough mixing of the component product to expose the entire product to light during illumination (light rays 65 are shown in FIG. 6). Thus, a substantially vertically disposed device 22 may have an advantage in using gravity for a substantial part of fluid movement, and only a bottom compartment squeezing element may be used.

Such turn over of fluid by mixing provides an advantage especially to pathogen reduction of relatively opaque substances such as RBC component products. With such products, light is not readily able to penetrate very deeply into the component product (e.g. not far past the bag film). Thus, the layer of blood product immediately adjacent the inner bag wall is irradiated, but should then be "turned over" or removed therefrom and replaced with a new layer of blood product which may then be irradiated. Mixing as described herein serves to "scrub" these bag wall layers of product away in desirable fashion. Moreover, such action may be made very aggressive during irradiation and help to shorten the pathogen reduction process.

Bag 35 is shown in FIGS. 3 and 4 and more particularly in FIG. 9 as constricted by clamps 27 only partially across the width thereof as limited by the lateral extensions of clamps 27. This may provide an advantage because it may provide additional lateral flows and mixing vortices as shown by arrows 58 in FIG. 9. Even so, and although thus far only partial constrictions have been shown and described extending from the outer border zones of the bag 35, it ought to be noted that such a bag could be divided more fully into two (or multiple) sub-compartments by placing one (or more) complete cross bar clamp assemblies over the bag at a desired location similar to the clamp assemblies shown in FIGS. 3 and 4, except that they might cover the entire width of the bag 35. Moreover, such a closure assembly could be an external removable openable assembly, an internal openable assembly, a clamp, a clip, or anything of the like which would entirely or partially divide the single container/bag into multiple sub-compartments though continuing to provide merely limited or constricted communication between the fluid contents contained within each separate sub-compartment such that flow is still viable therethrough as shown in FIGS. 6, 7 and 8. It is further noted that a number of alternative bag embodiments having one or more partial seals or welds, or other bag shapes such as those shown below in FIGS. 26 and 27 (see the hourglass shape therein) could be used as any bag including all of the bags or containers described herein. Otherwise, other mechanical closure (not shown) assemblies or resilient or even rigid containers with built in or external removable assemblies or other structural equivalents such as a clamp, a clip, a tongue and groove seal, a vise, a clasp, a grip, or a fastener may be used to create a narrowed portion within a container. These may be connected to device 22, 72, 92, 400, 500 or not, as may be desired.

Figure 10:
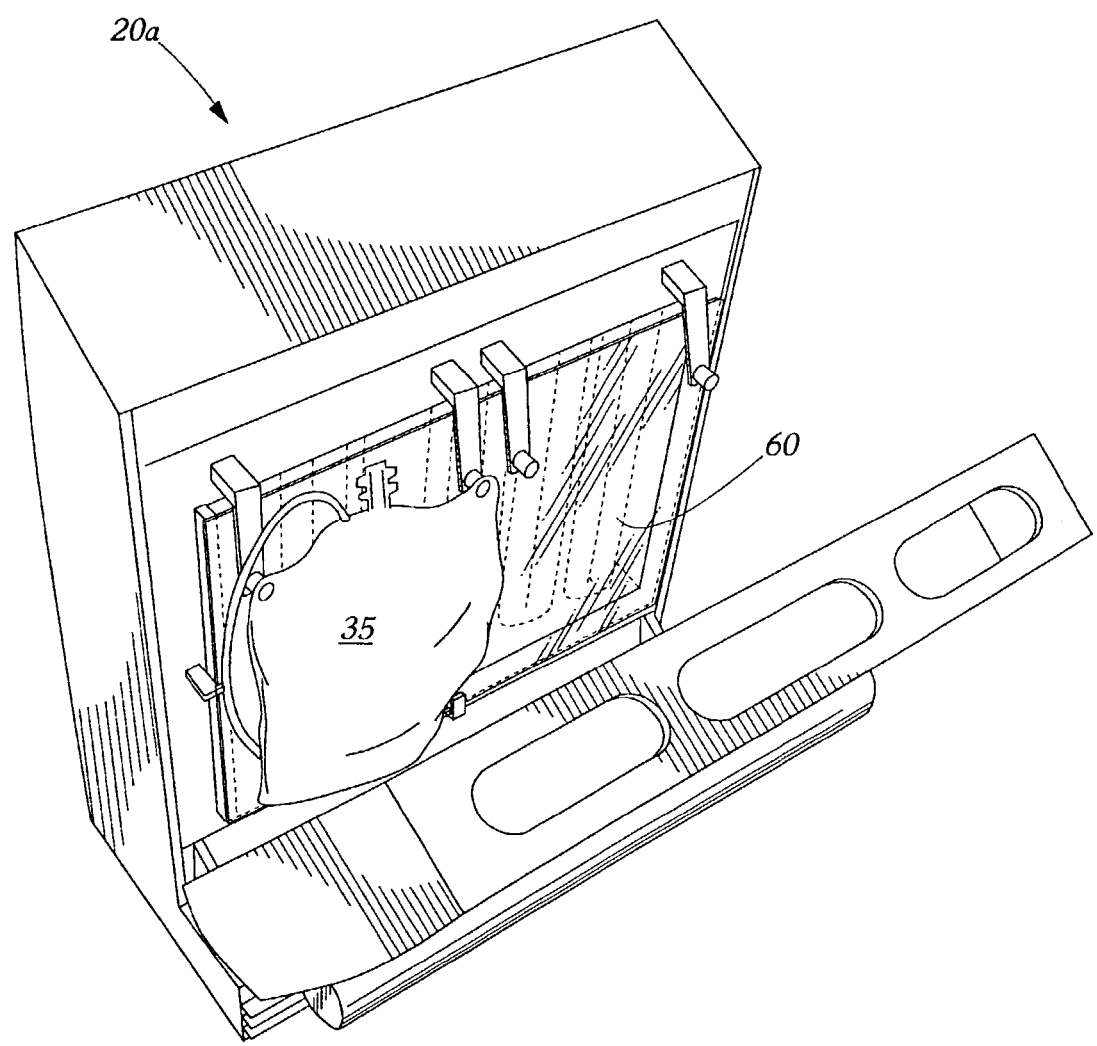
FIG. 10 shows an isometric view of an alternative mixing assembly.
Figure 11:
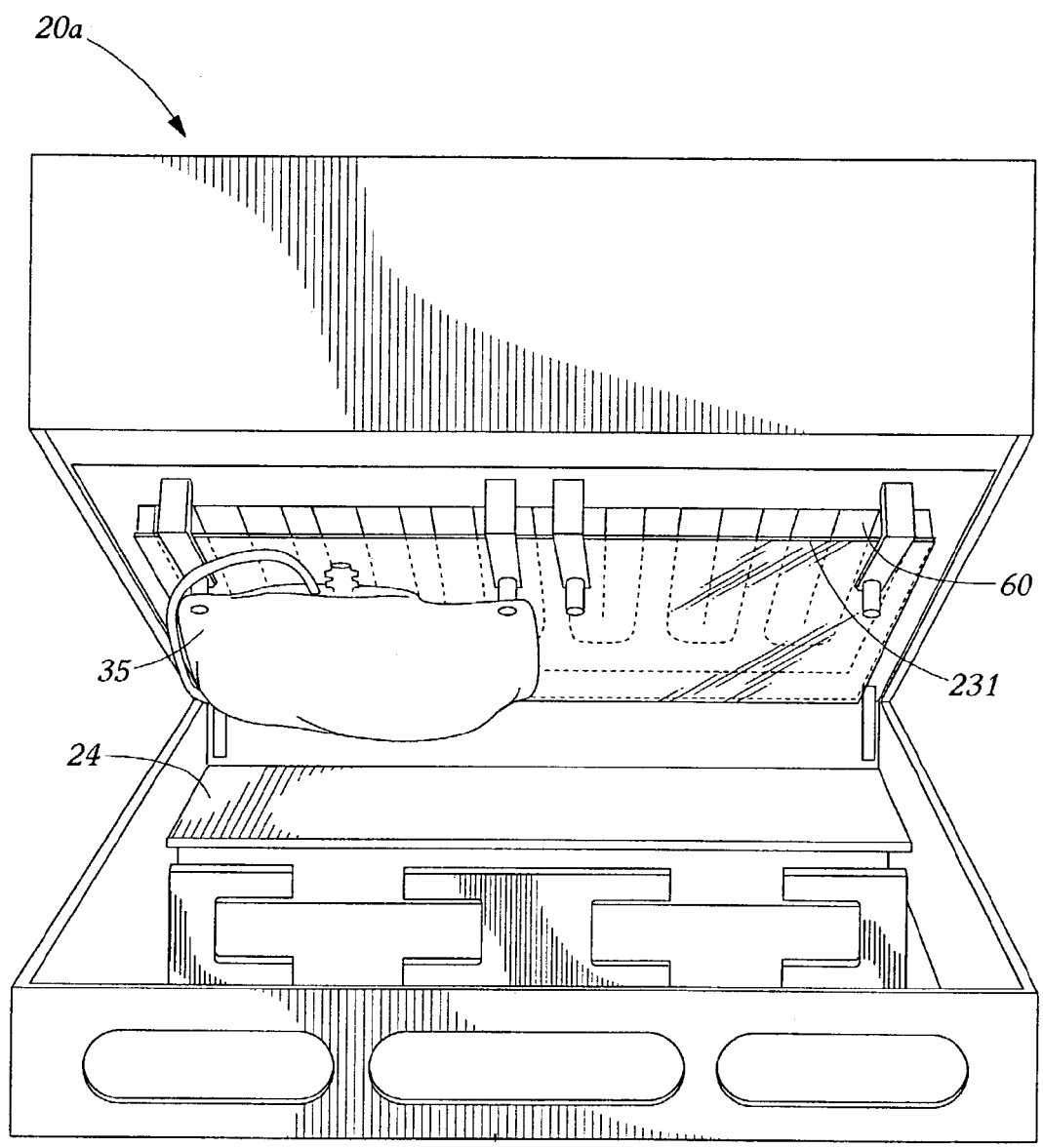
FIG. 11 shows a plan view of the alternative embodiment of a mixing structure according to FIG. 10.

Note, a primary embodiment using a squeezing device such as this could also make use of light sources (not directly shown as yet but see FIGS. 10 and 11) to shine on the bag, or multiple bags simultaneously (see the light rays 65 represented schematically in FIG. 6). Such an embodiment with a substantially vertically arranged squeezing or "clapping" mechanism is shown in FIGS. 10 and 11. Such a system 20a is shown having capacity for two bags though only one bag 35 is shown. In this embodiment two full length bars (not shown in FIG. 10) which stretch across the entire width of the two bags could be used one each on the front and back sides of the bags to create the clamping assembly 27 and associated mixing described in detail above. Here, however, at least one set of light sources 60 are shown which can be used to irradiate the bag(s) 35 and the contents thereof while mixing the contents using the motions and vortices described above. The contents may be fully exposed to photoradiation, and if a photosensitizer is used, such mixing would ensure proper exposure of the photoactivatable agent (e.g., riboflavin or psoralens) to the photoradiation, as well as to ensure fluid turn over. Note, though only one set of lights 60 are shown in FIGS. 10 and 11, another could be established on the opposing side of the bag(s) 35. Light radiation arrows 65 are shown in FIG. 6. A reflective surface to reflect the light throughout the chamber could also be used. The dashed line schematic light rays in FIG. 6 are intended to reflect these options (separate light sources or reflective surfaces). In any event, it may be preferred that light be made to impinge upon the bag(s) 35 from both sides (e.g. UV light, if used, may need to be provided from both sides). Note also that it may be advantageous for all or most of the physical elements touching or near bag(s) 35, e.g., the clapper structure 24 (see FIG. 11) and the back wall 231, to be transparent to light radiation, and may thus be made of a transparent polycarbonate, plexiglass, quartz glass or other sturdy substantially transparent material to allow light transmissivity therethrough. This may be advantageous in any or all embodiments described herein.

Figure 12:
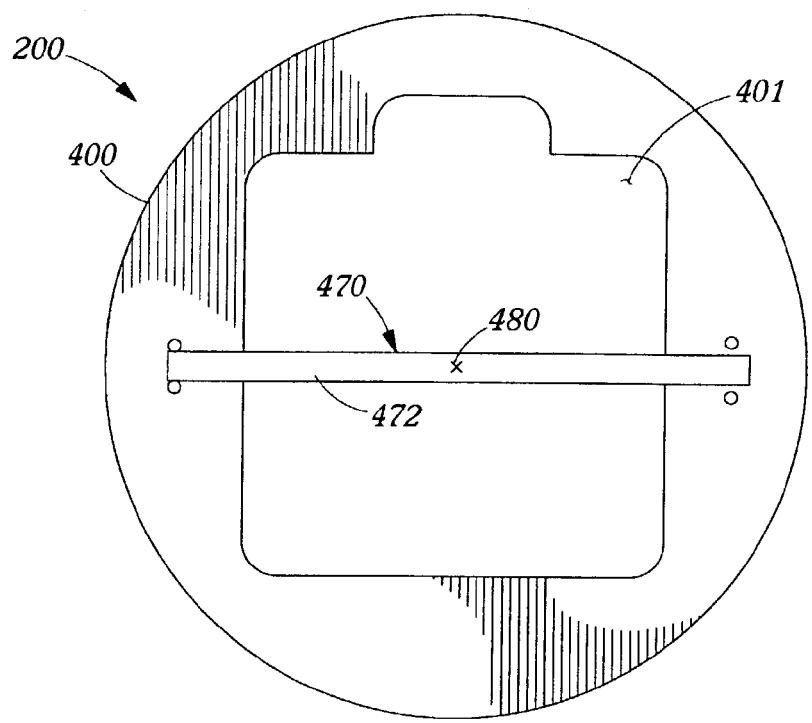
FIG. 12 shows an elevational view of another embodiment of a mixing structure and clamp.
Figure 13:
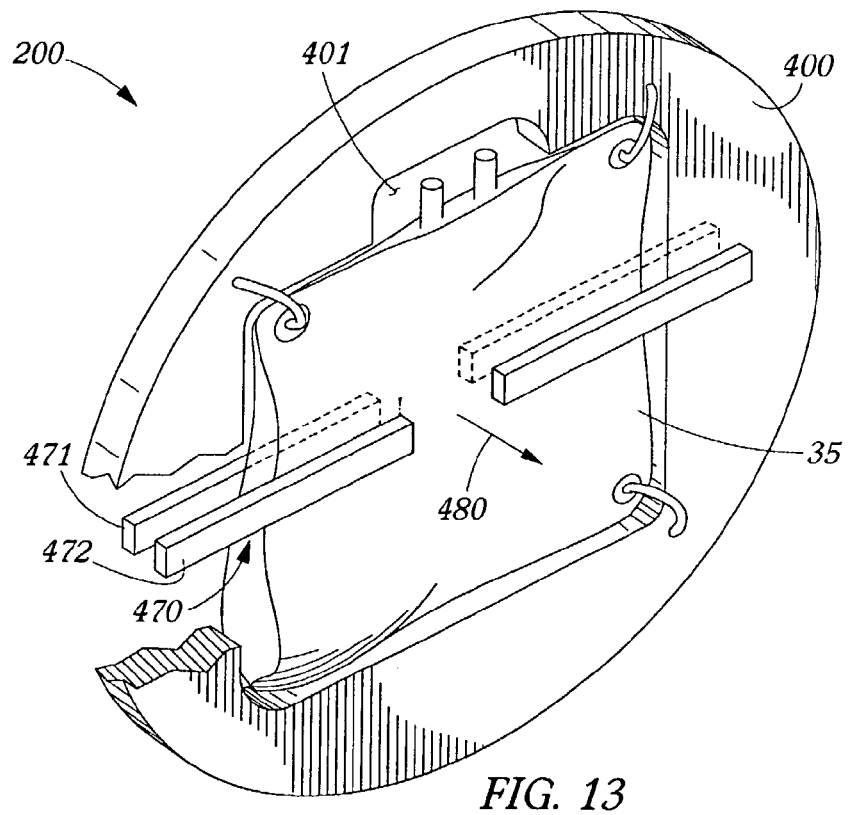
FIG. 13 shows a partially cut away isometric view of a mixing structure with a flexible container.

An alternative mixing structure may include a rotatable device or wheel in which a bag may be disposed. Shown in FIGS. 12 and 13 is a wheel 400 of a system generally designated 200. Wheel 400 has a cutout or aperture 401 defined therein in which a bag such as bag 35 (FIGS. 3–5) may be disposed. The cutout 401 where the bag 35 may be disposed, may be substantially transmissive to radiation. It is also contemplated that the cutout 401 may not be a cutout at all, but may be an indentation or well in the wheel 400 for holding the bag 35 to be irradiated. If this is the case, 401 may be made of material which is transparent to radiation, and may thus be made of a transparent polycarbonate, plexiglass, quartz glass or other sturdy substantially transparent material to allow light transmissivity therethrough. It is also contemplated that the indentation or well 401 may be made of material which is not transparent to radiation. The bag 35 may be clamped or otherwise held in place at four corners and/or along the sides at one or more locations with any of numerous alternative devices (not specifically shown). However, at least one bar or clamp device 470 is preferably used to provide the narrowed flow constrictions described above for the enhancement of mixing.

Preferably, as shown in FIG. 13, a bag 35 is disposed in the wheel 400 and constrained between two cross bar clamping members 471, 472 to squeeze or narrow the dimension therebetween for mixing. These may be disposed to divide the chamber of the container into approximate half or other sized portions. Then the wheel 400 is preferably disposed in an operably rotatable manner in a device (not shown) which will provide the rotating force to rotate the wheel 400 about its central axis 480 (FIG. 13). In one embodiment, the rotation will be ±360 continuous degrees with light shining at the bag from both sides of the bag/wheel. In one embodiment, the wheel may be rotated in an alternating fashion in one direction for a period of time, and then the wheel could be reversed to rotate in the other direction for a period of time. Gravity is used to first pull the contents of the bag 35 down into the lower portion of the bag 35, and as the bag is rotated and turned or flipped over, gravity pulls the contents down into what was the upper portion, now inverted and disposed under the previous lower portion (FIG. 6). Upon continued rotation, the bag is re-inverted so that the original upper portion is once again disposed above the original lower portion and gravity pulls the contents again down into this lower portion (FIG. 6). As shown in FIG. 6, upon each inversion, the flow of contents passes through a constriction 55 between clamping members 471, 472 et al. and creates mixing as depicted. Such mixing again provides for scrubbing the inner bag surface to ensure removal of already irradiated material therefrom and ensures that new material not yet irradiated is deposited there so that the newly deposited material may be exposed to light.

Figure 14:
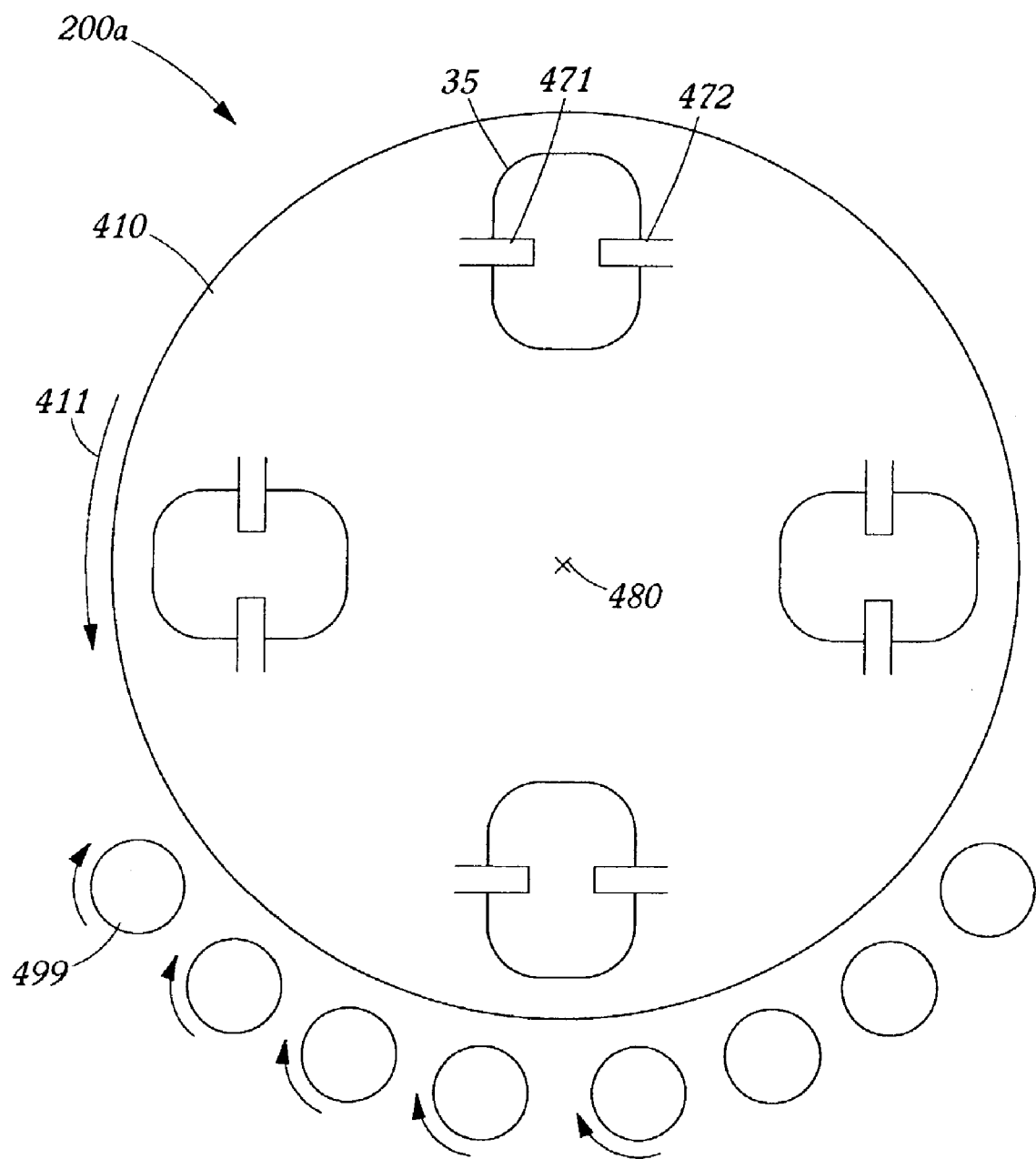
FIG. 14 shows an elevational view of an alternative embodiment mixing structure somewhat like that in FIGS. 12–13.

Another version 200*a* of a wheel 410 is shown in FIG. 14 in which multiple (here, four (4)) bags 35 are shown disposed thereon for rotation with the wheel 410. Clips or clamps 471, 472 are also shown for holding the bags and/or providing the flow constrictions for mixing as described throughout. Rollers 499 are shown schematically as one alternative for providing the motion necessary to rotate wheel 410 (or 400, see FIGS. 12, 13). Thus, such rollers could be disposed in a device (not shown but not unlike that shown in FIGS. 10, 11) and be mechanized to roll in a direction similar to that shown in FIG. 14 to provide a rotational motion to the wheel 410 designated by the arrow 411 in FIG. 14, and thus the wheel and bag(s) may be rotated and the contents thereof mixed while also being exposed to photoradiation. Note, though not shown in these rotating wheel embodiments, light sources may be used to shine light on one or the other, or in some embodiments, both sides of a rotating bag for photoactivation of photosensitizer chemicals in the bag, if used. Such lights may be disposed in banks on either side of the respective bag. These banks may thus be stationary relative to the rotating/moving bag (see FIG. 10) and/or wheel device such as wheel 400 (or 410, inter alia), or the light banks may be made to rotate with the bag. As an example of this please see the further alternative wheel embodiment as shown in the embodiments of FIGS. 15–18.

Figure 15:
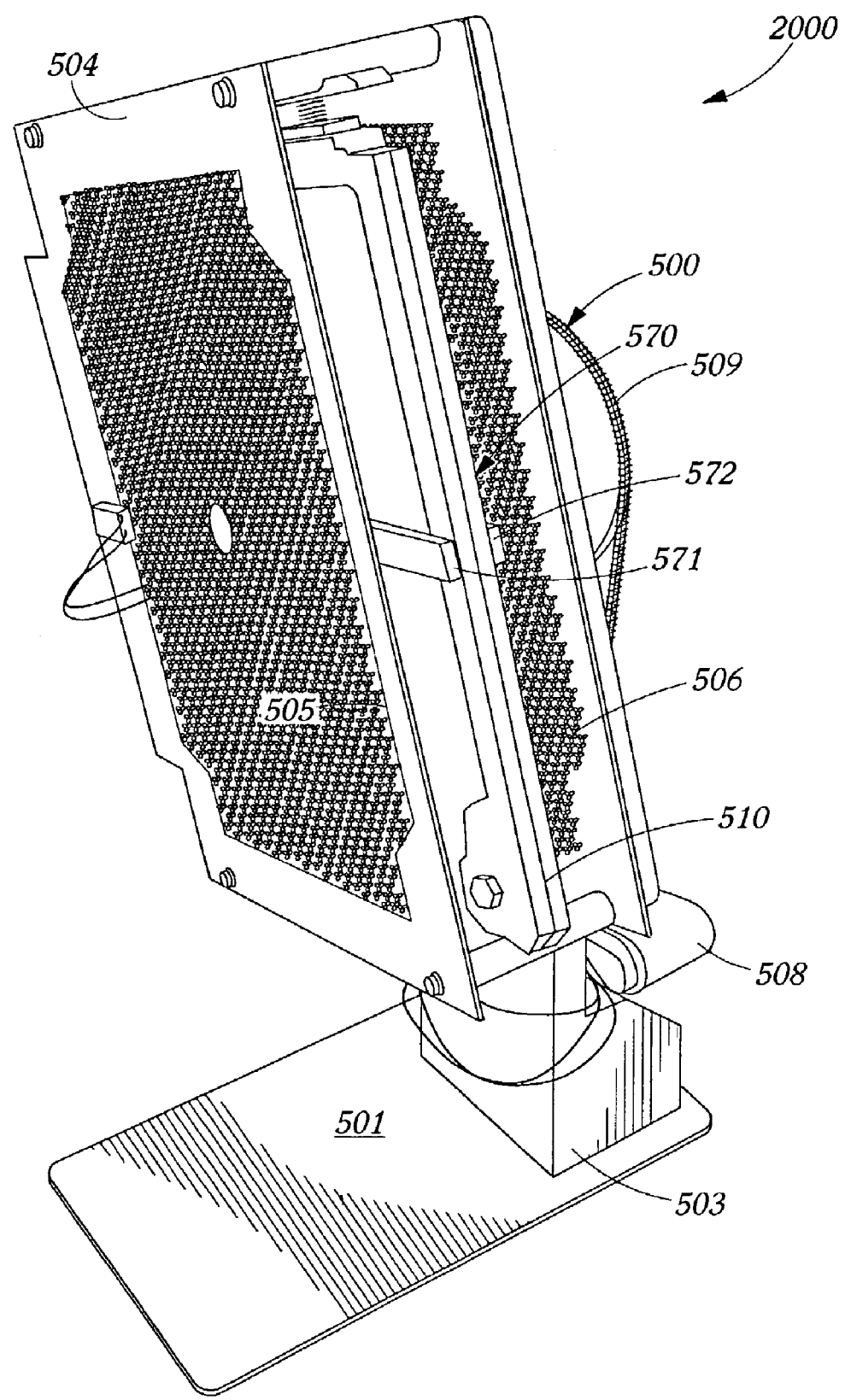
FIG. 15 shows an isometric view of an alternative embodiment of a mixing structure according to the present invention.
Figure 16:
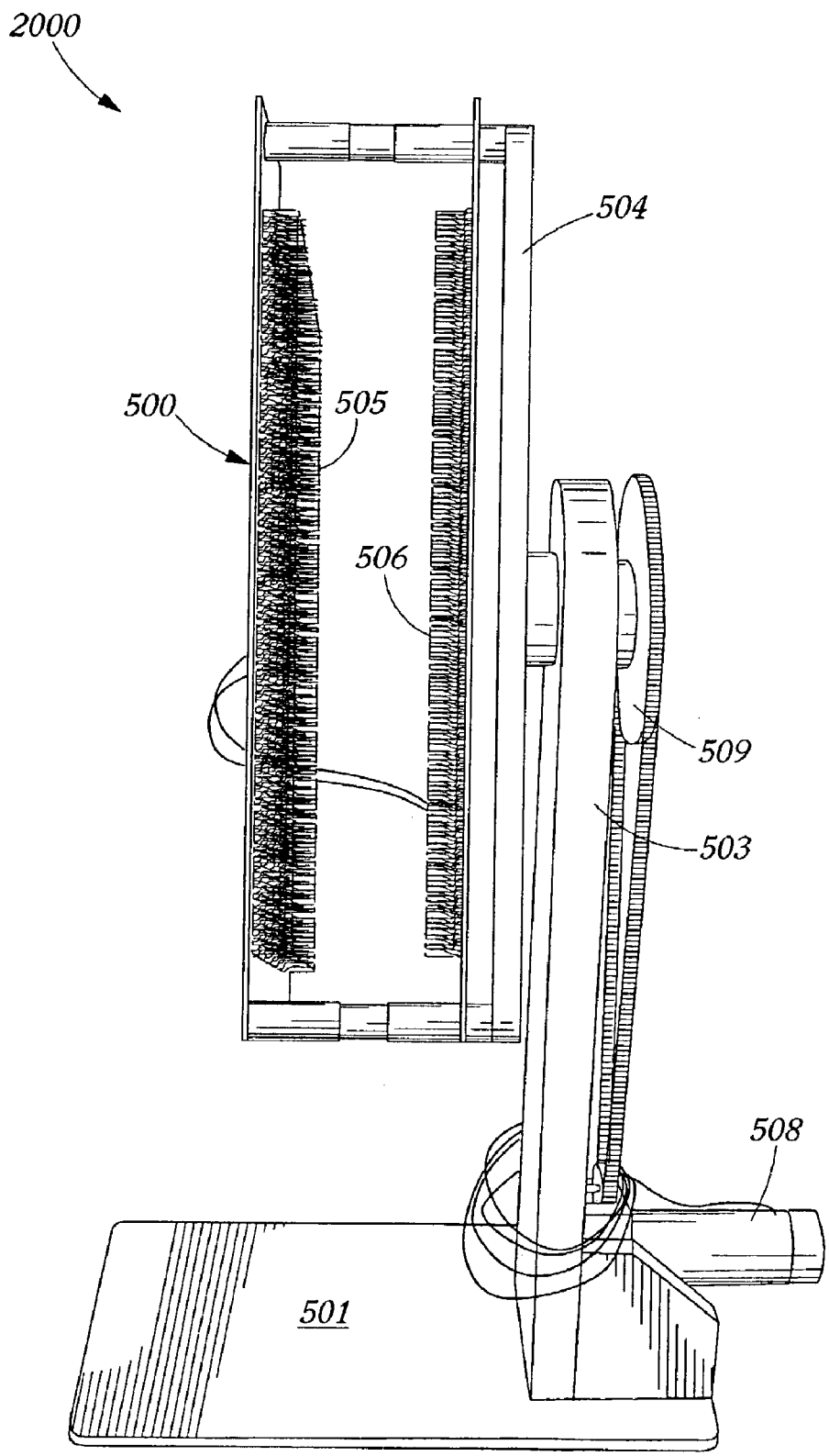
FIG. 16 shows a side elevational view of the alternative embodiment of FIG. 15.
Figure 17:
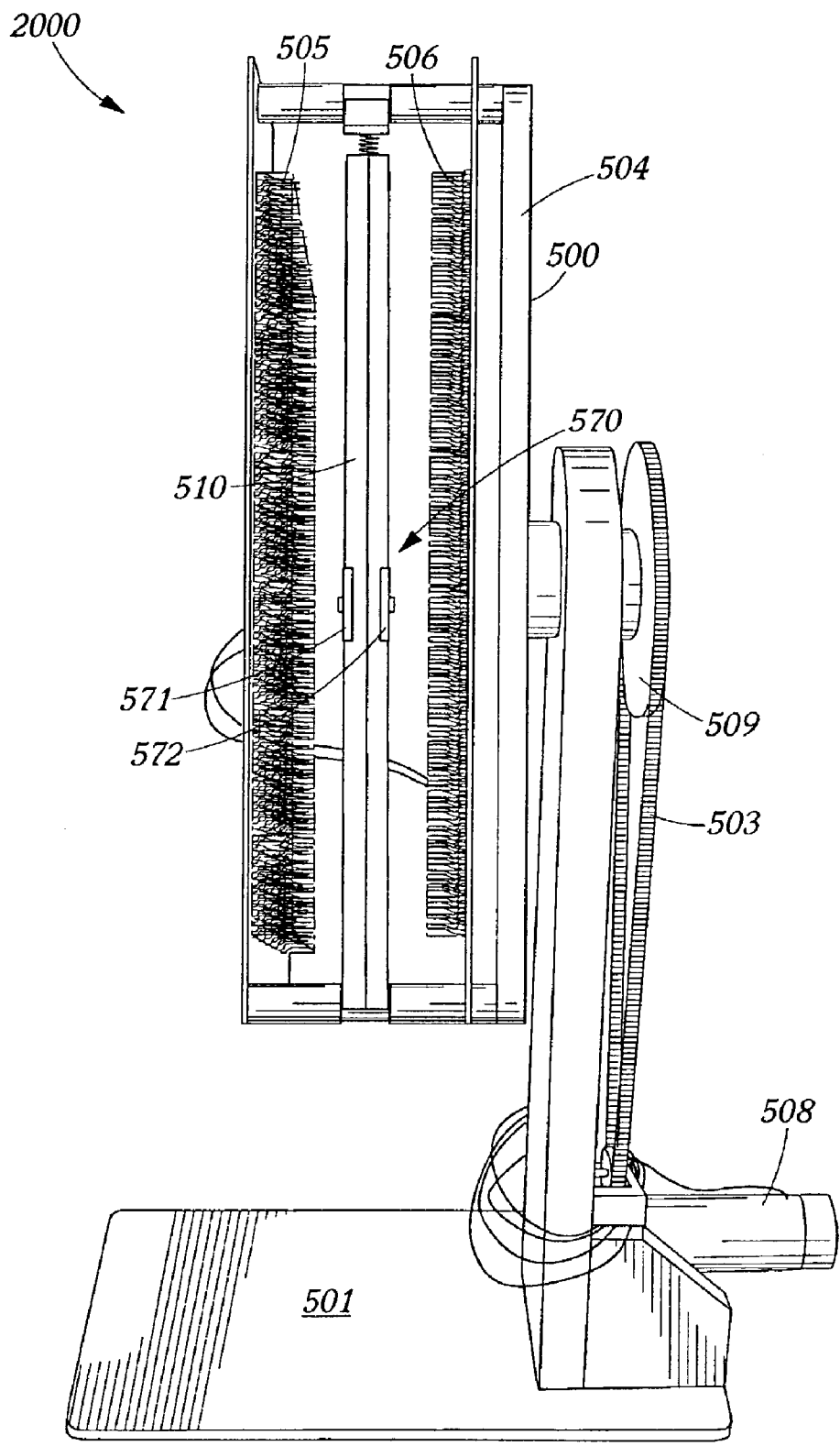
FIG. 17 shows another side elevational view of the embodiment of FIG. 15.
Figure 18:
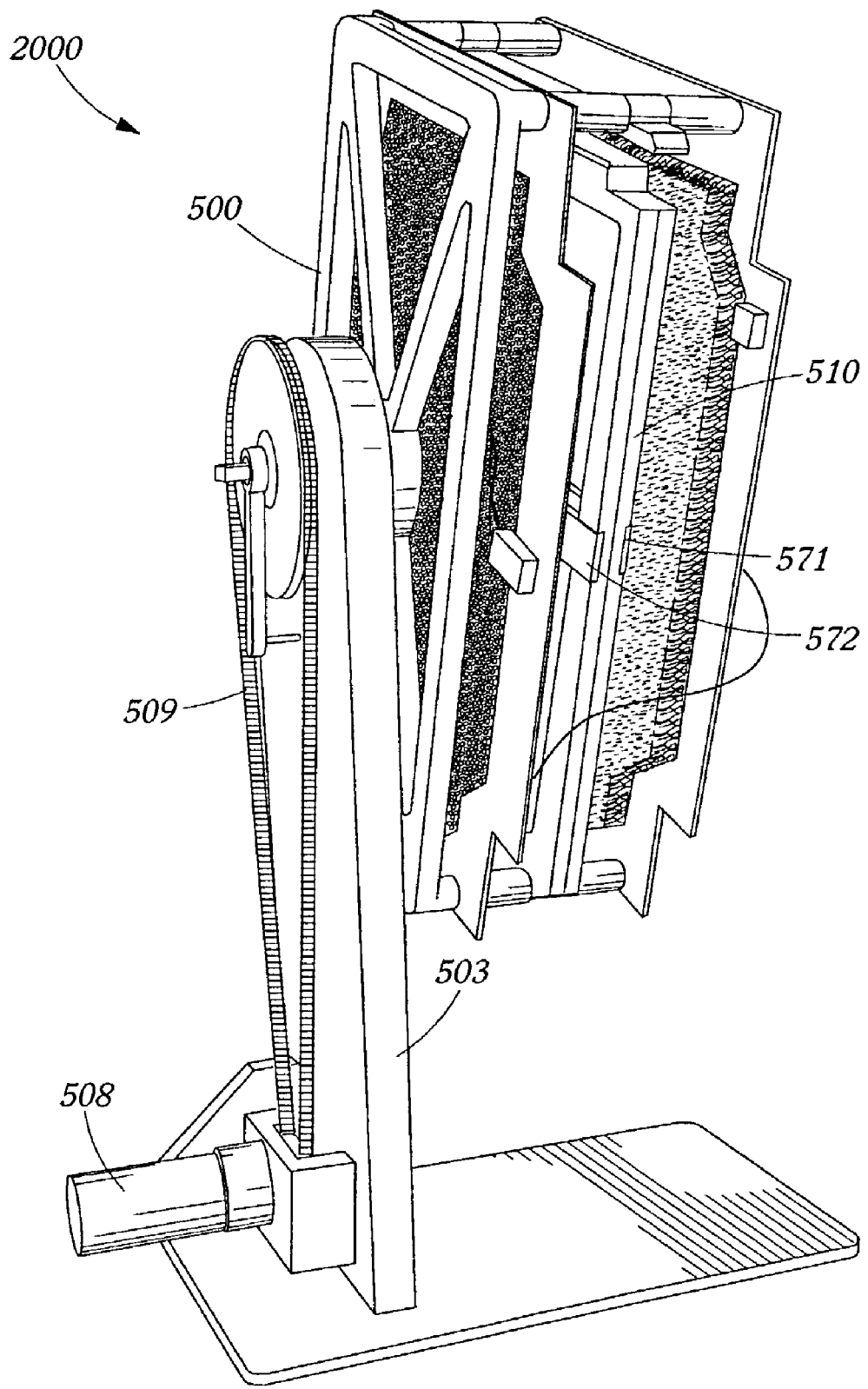
FIG. 18 shows a rear isometric view of the embodiment of FIG. 15.
Figure 19:
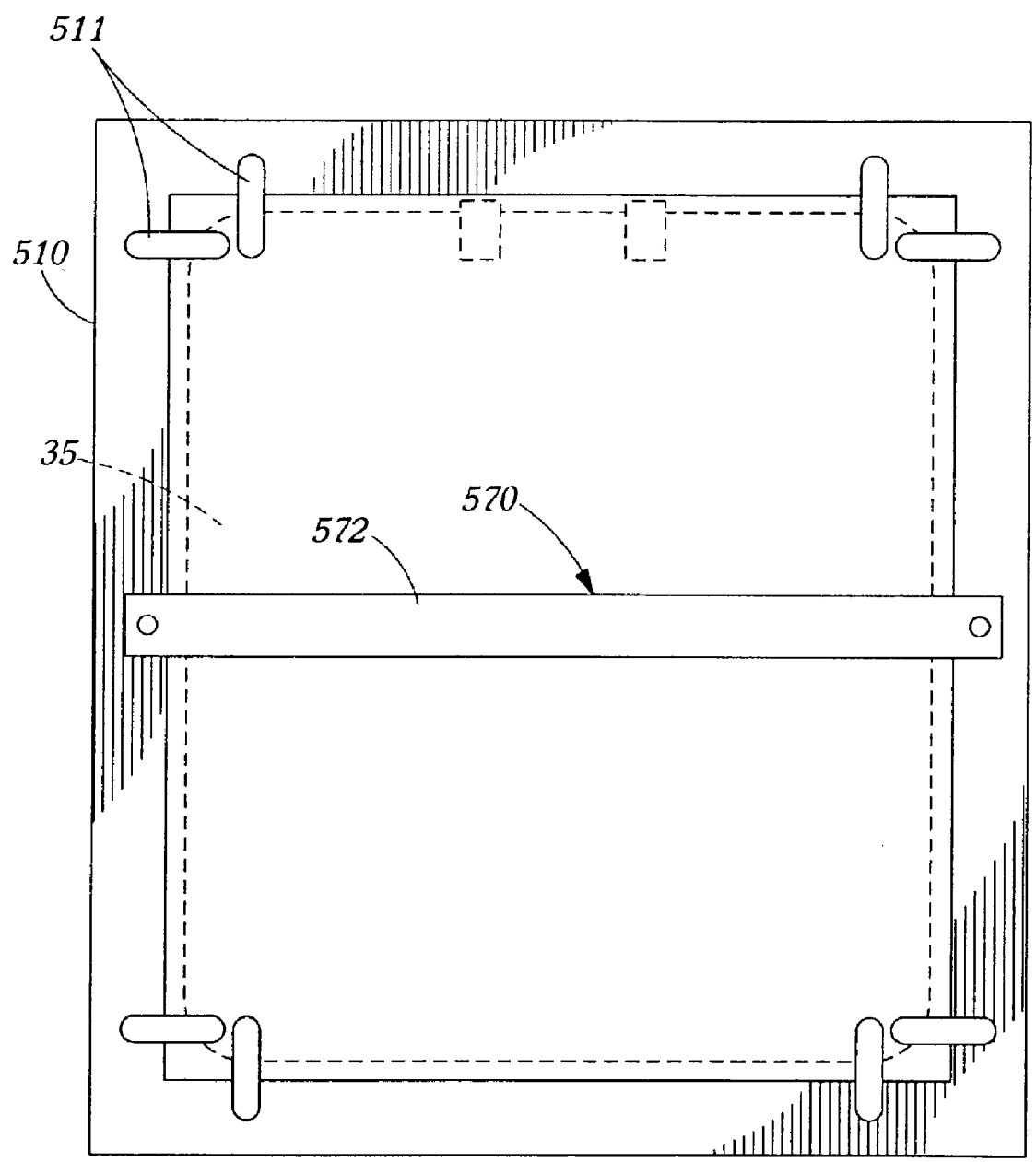
FIG. 19 is a plan view of a frame for use with the embodiments of FIGS. 15–18.

In the embodiment of FIGS. 15–18, a system 2000 is shown with a device 500 which includes a base 501, a support arm 503 and a rotatable member 504 which here includes front and back light banks 505, 506 which are thus rotatable. A motor 508 with a chain link style gear driving mechanism 509 is also show in FIGS. 15–18 (particularly FIG. 18). A frame 510 which is adapted to hold a bag 35 (as shown in FIG. 19, see below) is shown as disposed in device 500 in FIGS. 15, 17 and 18 (FIG. 16 shows device 500 without frame 510). Thus, when a bag 35 is disposed in a frame (see FIG. 19), and frame 510 is disposed in device 500, the motor 508 can be activated to turn the gear assembly 509 which in turn rotates the rotatable member 504 with light banks 505, 506 and frame 510. A mixing action of contents in bag 35 like that shown and described relative to FIG. 6 then occurs.

As shown in more detail in FIG. 19, a bag 35 (shown in dashed lines), held in place by clips/clamps/hooks 511, may also be crossed by a crossbar clamping assembly 570 which includes a cross bar member 572 which provides a flow constriction for mixing like that shown in FIG. 6. It should be noted that constriction element 570 extends the entire length of the bag, however, constriction element 570 may also extend partially across the bag such as the constriction elements shown in FIGS. 3 and 13. A corresponding bar 571 is shown in FIGS. 15, 17, and 18 on the opposing side of the frame 510.

Thus, when rotated and illuminated, a pathogen reduction process can be achieved. In this embodiment, the irradiation source is shown as being LEDs (light emitting diodes). One advantage in using LEDs is their ability to be located in close proximity to the bag containing fluid to be pathogen reduced without emitting much heat, which could damage the blood or blood component being irradiated. LEDs are also useful in this invention because they emit light in very narrow bandwidths. Light in a narrow spectrum may be beneficial to the blood product being irradiated because all non-useful wavelengths of light which might damage the blood or blood components are eliminated.

Figure 22:
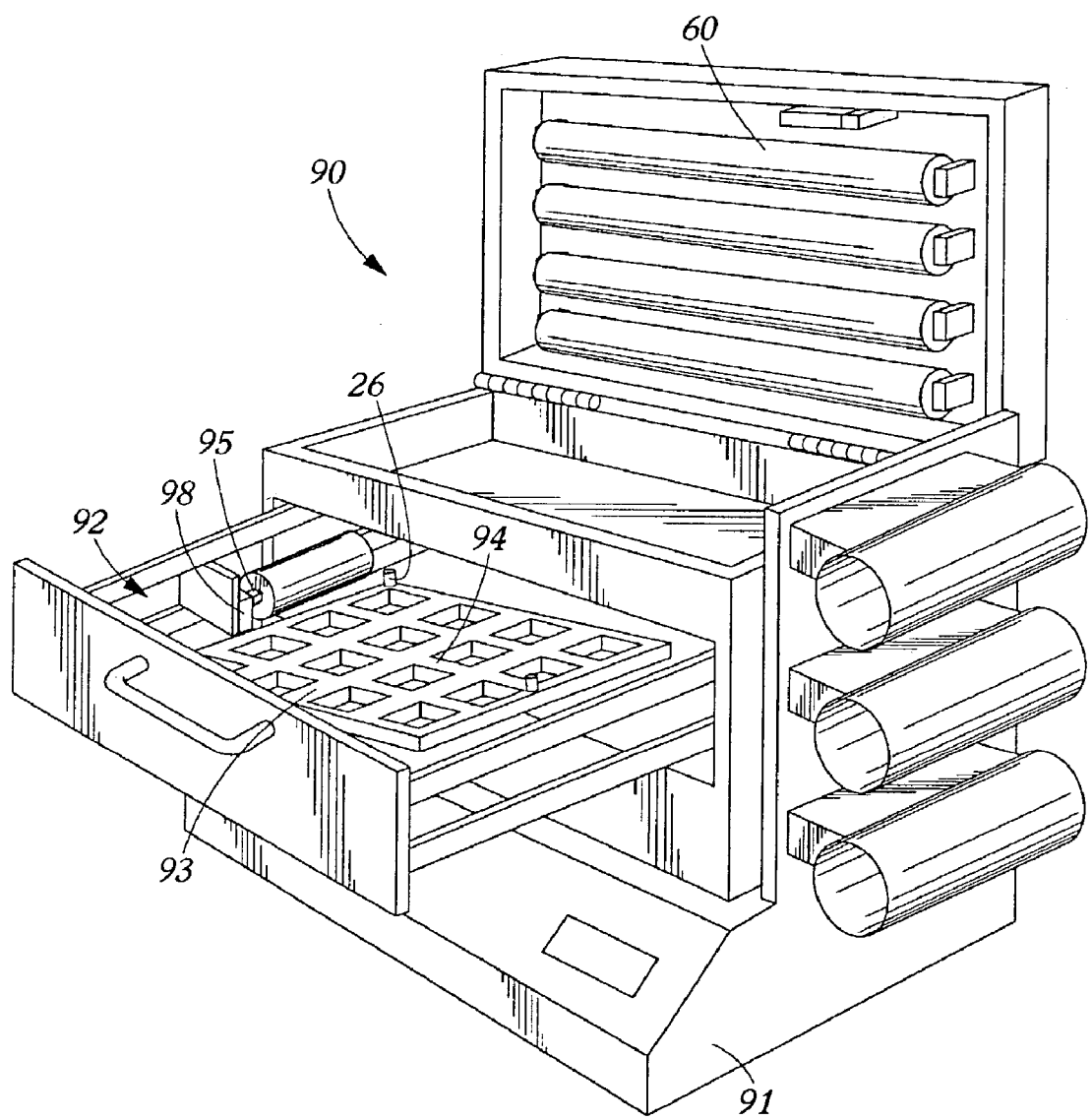
FIG. 22 is an isometric view of another alternative embodiment of the present invention.

Fluorescent bulbs may also be used as the irradiation source (see FIGS. 10 and 22). Visible or ultraviolet light may be used, depending on the type of blood or blood product to be pathogen reduced as well as the type of photosensitizer to be used, if any.

Note, in the rotatable examples, more resilient or even rigid containers may be used. Constriction elements which are built in or completely removable may also be used in these embodiments.

Figure 20:
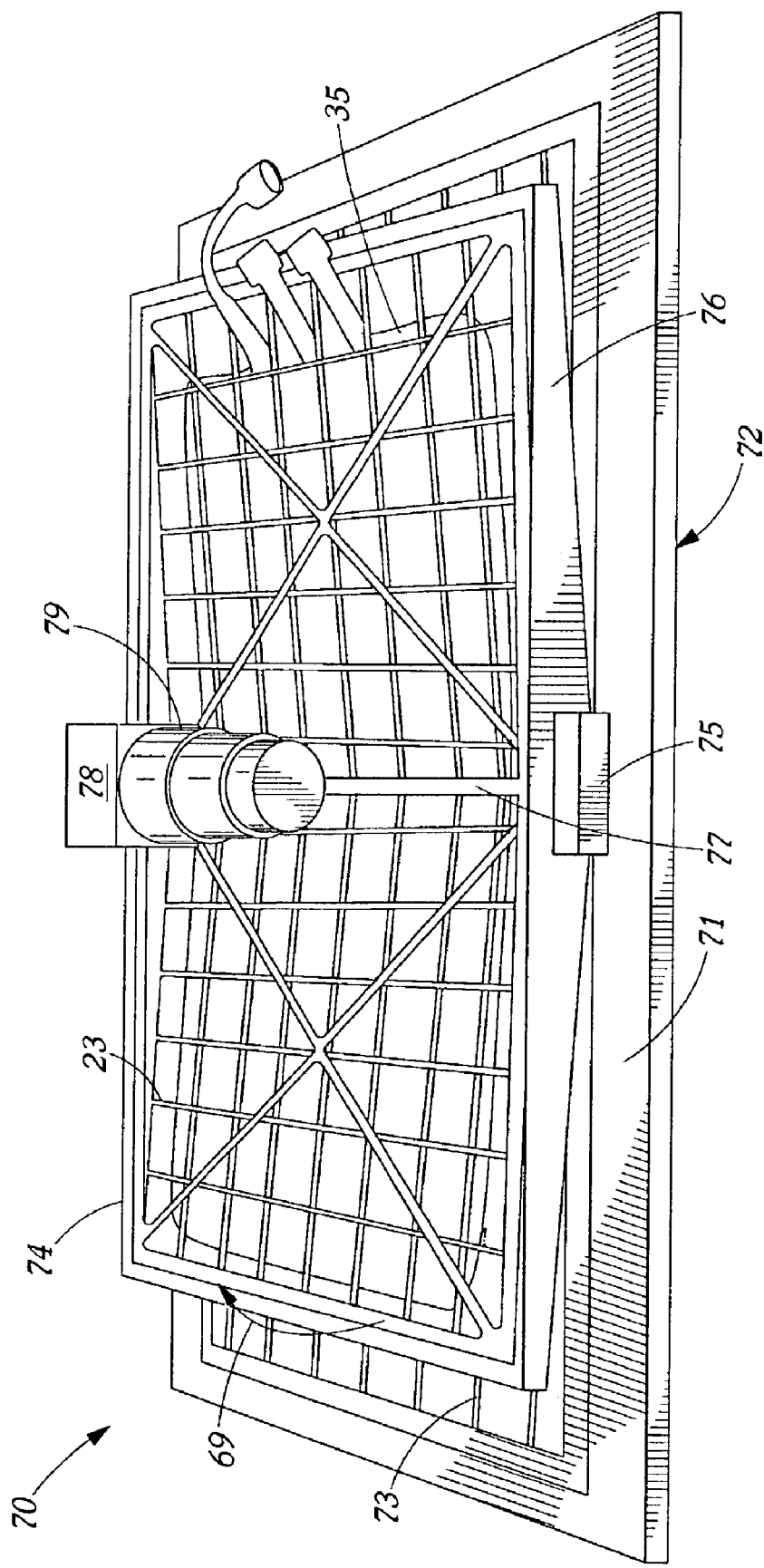
FIG. 20 is an isometric view of an alternative embodiment of the present invention.
Figure 21:
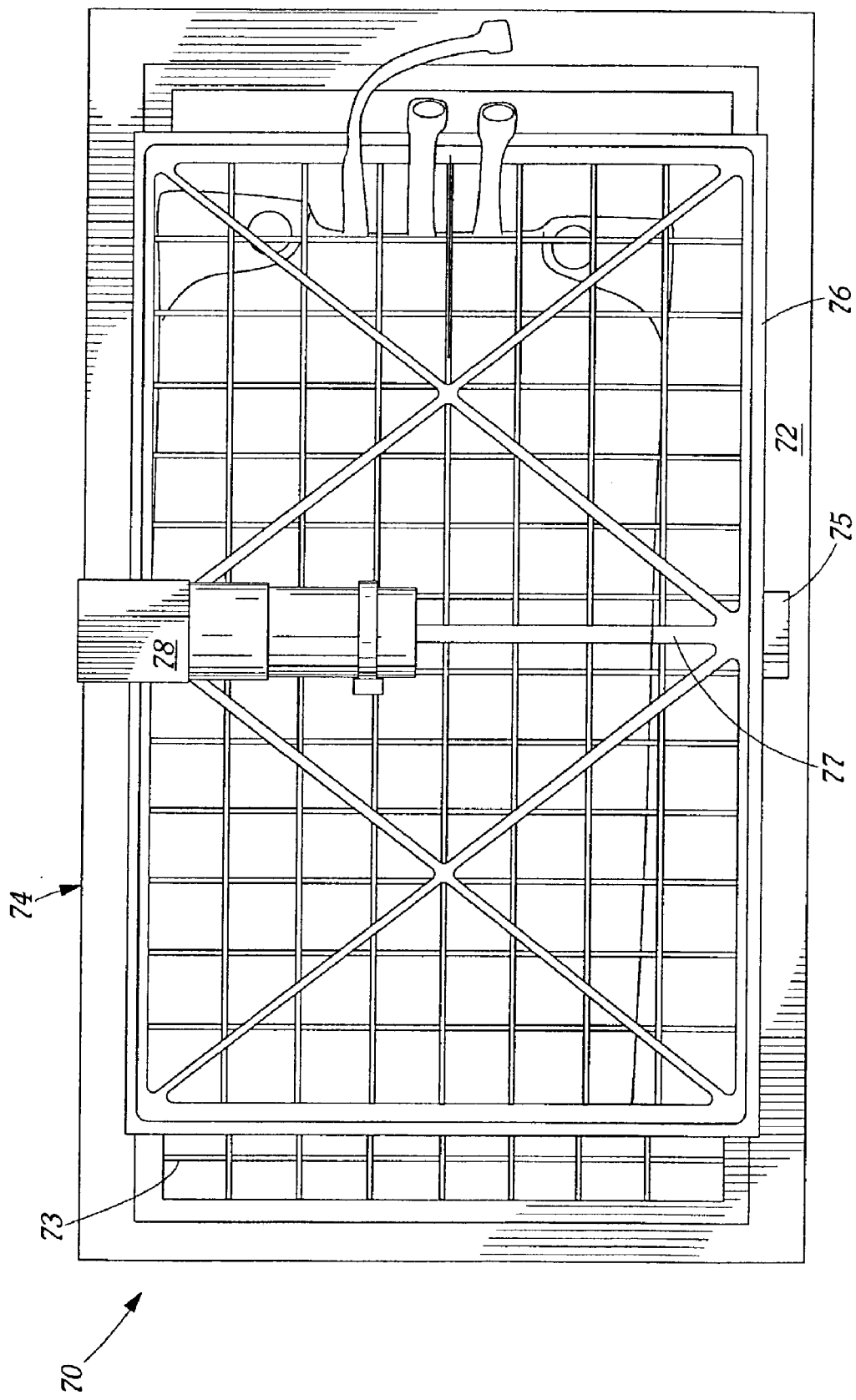
FIG. 21 is a top plan view of the embodiment of FIG. 20.

Further embodiments may include other than the substantially vertical embodiments described heretofore (which take advantage of gravity as a flow forcing element therein). For example, substantially horizontal-mixing structures may also be used. A first such embodiment is shown in FIGS. 20, 21. The system 70 of FIGS. 20, 21 includes a mixing device 72 which may include a base frame 71, to and/or in which may be a screen-like support 73 on which a bag 35 may be disposed (note, metal or transparent plastics may be used). A rotatable squeezing or clapping assembly 74 may then be disposed in operative relationship therewith. Assembly 74 is connected via a pivot assembly 75 to the frame 71 assembly in relative central position and preferably has one or two flappers 76 which may be moved down onto and squeeze the bag 35 when this is disposed therein. A motor 78 may be used to impart the back and forth rotational movement, through motor connection 79, to the rotatable assembly 74. Back and forth rotation hereof is generally shown by the arrows 69 (FIG. 20.) A constriction or clamp member 77 may also be used herewith. Indeed, constriction member 77 may be a part of the rotation connection assembly, as for example, an axle which may lay across the bag 35, again in a substantially central location. A corresponding upraised portion or member (not directly shown) may be disposed on the underside of bag 35 as perhaps a portion of or a member connected to the support structure 73. A further alternative in this or any of the embodiments in this specification, is to use a separate clamping assembly (not separately shown), not directly attached to the device 72. In any case, it may be preferred (though not necessary) to have a constriction device in order to provide the mixing action shown and described relative to FIG. 6 above.

Note, as introduced above this system 70 can be disposed substantially horizontally, so long as there is access to lights if so desired, and in an embodiment these could be shining from both top and bottom sides (although one side or the other may also be operable). Even so, it could also be disposed vertically or in numerous other dispositions in three-dimensional space.

A further usually substantially horizontally disposed embodiment is shown in FIGS. 22, 23, 24 and 25 (although this also could be disposed in any number of other dispositions in 3D space). In the primary embodiment shown in FIG. 22, the system 90 is shown which includes an irradiation unit 91 in which is disposed a mixing device 92. Device 92 includes a moveable tray or frame 93 with a screen or other support 94. As shown in more detail in FIG. 23, the movable tray 93 may be connected by a pivot assembly 95 to a motor 98 which may provide the movement for mixing the contents of the bag 35 which may be disposed thereon (see FIGS. 24 and 25, described below). In one embodiment, a clamp device 97 (see FIGS. 24–25) may be also included to provide flow-mixing vortices as shown and described both above and below.

As shown in FIG. 24, the moveable tray 93 may be moveable back and forth in a lateral or longitudinal type of motion or both. This is shown by the lateral arrows 101. This can then create the fluid flow vortices identified by the flow arrows 102 inside bag 35.

Similarly, as shown in FIG. 25 the tray may also be rotated slightly to cause fluid motion in the bag 35. This rotation is shown by arrows 103 and the fluid flow vortices created thereby are shown by arrows 104 in the bag 35. Note, the tray 93 may rotate in either or both lateral or longitudinal rotations (e.g., rotations about lateral or longitudinal axes). Lateral rotations are shown by arrows 105 (FIG. 23.) The movements such as the back and forth lateral or longitudinal movements (as shown in FIG. 24) may be combined with rotations in other directions (as in the lateral and/or longitudinal rotations as shown in FIG. 25), and may be in either ordered or random combinations. Thus wobbles and/or nutations (as from wobbulators or nutators, as known) may be further alternatives included here as well. Still further rotations may be circular or elliptical or other orbital movements, as depicted generally by the arrows 107 in FIG. 23. Such orbital motions may be used in lieu of or in addition to those previously described. Churning, undulating, oscillating, gyrating, shaking and/or stirring are but a few of a host of other motions which may be performed here within one, two or three dimensions, alone or in combination to provide mixing according to this invention.

FIG. 26 shows another embodiment of a flexible container which may be used in/with the present invention (squeezing or rotation, or mere movement) wherein the flow constriction assembly is a part of the bag/container 350. The container 350 may be made of polymeric type film material extruded in a tube-like shape. The main body compartment of container 350 has two partial seals or welds 370 which at about half way up the length of the main body compartment extend inwardly from the sides of the container 350. The partial seals or welds 370 divide the main body portion into two partial sub-compartments 351, 352 respectively. Although shown as extending inwards from the sides of container 350, one or more partial seals or welds 370 may extend from any of the four sides of the bag 350 without departing from the spirit and scope of the invention. These partial seals or welds 370 are intended to provide vortices 58 in the fluid during the mixing process.

FIG. 27 shows a plan view of another alternative embodiment of a further polymeric container 3500 which may be used in/with the present invention. This container 3500 may be made of a polymeric type film such as PVC or polyolefin (flexible or not). The container may be sealed or welded around its outer border zones during manufacture. The seals or welds create a fluid tight, sealed interior space. The container is configured in a substantial figure eight or hourglass shape as shown (and as introduced above). The container 3500 has an upper expanded interior or sub-compartment portion 3510, and a lower expanded interior portion or sub-compartment 3520. The upper expanded sub-compartment 3510 and the lower expanded sub-compartment 3520 are connected to each other in a fluidly communicative relationship by narrowed portion 3555 defined by the indented sides of the container. Both the upper expanded sub-compartment 3510 and the lower expanded sub-compartment 3520 may also be further subdivided into multiple sub-compartments (not shown) without departing from the spirit and scope of the invention. As shown in FIG. 27 a constriction 3700 is formed by the figure eight or hourglass shape in such a fashion so as to divide bag 3500 into two separately contained fluid-tight or fluidly separated sub-compartments 3510, 3520. Sub-compartment 3510 is located above sub-compartment 3520.

As shown in FIG. 27, the figure eight or hourglass configuration may aid in mixing the solution within the bag 3500. The fluid in the bag may be mixed in a substantially vertical manner or a substantially horizontal manner and/or any angle therebetween (although a vertical disposition will have gravity assistance). A force imparted to the bag at a particular location creates the movement of fluid within the bag. As the fluid is forced to move through the narrowed portions 3555 of the hourglass/figure eight shape, vortices 58a are created within the fluid which helps to further mix the fluid. A clamp (not shown) such as those described herein may also be used to create narrowed portions within the bag. A seal or weld like a clamp structure could also be used to further separate any portion into two smaller sub-compartments and may thus also assist in creating further vortices within the fluid. The narrowed portion or portions create vortices within the fluid as the fluid is forced to flow through the narrowed portions as described throughout.

FIG. 27 shows the bag 3500 in the figure eight or hourglass configuration being mixed by clapping or rotation in either a substantially vertical and/or a substantially horizontal manner. If rotated, the bag may be rotated about its centerpoint (not shown) between about 1500 and about 3600 in a continuous fashion. A force (from the rotation itself and/or due to the force of gravity when in a vertically disposed embodiment) may be imparted to the bag by virtue of the rotation of the bag to create the initial movement of fluid within the bag. As the fluid is forced to move around the figure eight or hourglass shape, vortices are created within the fluid which helps to further mix the fluid. The bag may be rotated in a continuous manner, or may be agitated in varying degrees from between about 0° to about 360° without departing from the spirit and scope of the invention. The bag may also be rotated either singly or in a repetitive manner.

The examples of the above-described systems, methods, and apparatuses and bags are for illustrative purposes only. Because of variations which will become apparent to those skilled in the art, the present invention is not meant to be limited to the particular embodiments described above. Any such variations and other modifications or alterations are included within the scope and intent of the invention.

The invention claimed is:

1. A mixing system for use in mixing a fluid contained within a fluid container, the system comprising:
   a support structure;
   at least one movable squeezing element operably disposed relative to the support structure;
      wherein the moveable squeezing element is a moveable clapping member;
   a holding device adapted for holding the fluid container between the support structure and the movable squeezing element;

an irradiation source for irradiating the fluid contained within the fluid container; and whereby the movable squeezing element is adapted to move so as to squeeze the fluid container against the support structure to thereby mix the fluid contained in the fluid container.

2. The mixing system according to claim 1 wherein the irradiation source irradiates the fluid while the fluid contained in the fluid container is thereby mixed.

3. A mixing system according to claim 1 in which the fluid to be mixed is whole blood.

4. A mixing system according to claim 1 in which the fluid to be mixed is a blood component.

5. A mixing system according to claim 1 in which the fluid to be mixed includes a pathogen reduction agent.

6. A mixing system according to claim 5 in which the pathogen reduction agent is a photosensitizer.

7. A mixing system according to claim 6 in which the photosensitizer is riboflavin.

8. A mixing system according to claim 6 in which the photosensitizer is a psoralen.

9. A mixing system according to claim 1 which further comprises a motor which is operably connected to the movable squeezing element to move the movable squeezing element.

10. A mixing system according to claim 9 in which the motor moves the movable squeezing element in a reciprocal motion, closed and open to alternately squeeze and release the fluid container.

11. A mixing system according to claim 1 in which the movable squeezing element is rotatable about a pivot point.

12. A mixing system according to claim 1 which further comprises a constriction element disposed in operative relationship with the fluid container.

13. A mixing system according to claim 12 in which the constriction element provides a narrowed fluid flow passage within the fluid container which thereby provides a vortex action of fluid being moved therein.

14. A mixing system according to claim 12 in which the constriction element is a clamp.

15. A mixing system according to claim 14 in which the clamp is removably connected to the support structure.

16. A mixing system according to claim 14 in which the clamp is permanently affixed to the support structure.

17. A mixing system according to claim 12 in which the constriction element is a feature of the container.

18. A mixing system according to claim 17 in which the feature of the container is a welded seam.

19. A mixing system according to claim 17 in which the feature of the container is a side indentation.

20. A mixing system according to claim 1 in which the fluid container is a flexible bag.

21. A mixing system according to claim 1 in which the fluid container is a substantially resilient container.

22. A mixing system according to claim 1 in which the irradiation source provides ligbt to at least two sides of the fluid container.

23. A mixing system according to claim 1 in which the fluid container is held in a substantially vertical orientation.

24. A mixing system according to claim 1 in which the fluid container is held in a substantially horizontal orientation.

* * * * *